US011667592B2

(12) United States Patent
Berlinguette et al.

(10) Patent No.: US 11,667,592 B2
(45) Date of Patent: Jun. 6, 2023

(54) METHODS AND APPARATUS FOR PERFORMING CHEMICAL AND ELECTROCHEMICAL REACTIONS

(71) Applicant: THE UNIVERSITY OF BRITISH COLUMBIA, Vancouver (CA)

(72) Inventors: Curtis Berlinguette, Vancouver (CA); Rebecca Sherbo, Vancouver (CA)

(73) Assignee: The University of British Columbia, Vancouver (CA)

( * ) Notice: Subject to any disclaimer, the term of this patent is extended or adjusted under 35 U.S.C. 154(b) by 186 days.

(21) Appl. No.: 16/964,944

(22) PCT Filed: Jan. 25, 2019

(86) PCT No.: PCT/CA2019/050097
§ 371 (c)(1),
(2) Date: Jul. 24, 2020

(87) PCT Pub. No.: WO2019/144239
PCT Pub. Date: Aug. 1, 2019

(65) Prior Publication Data
US 2021/0040017 A1  Feb. 11, 2021

Related U.S. Application Data

(60) Provisional application No. 62/622,305, filed on Jan. 26, 2018.

(51) Int. Cl.
*C25B 1/02* (2006.01)
*C25B 3/23* (2021.01)
(Continued)

(52) U.S. Cl.
CPC ................ *C07C 5/09* (2013.01); *C25B 1/02* (2013.01); *C25B 3/23* (2021.01); *C25B 9/19* (2021.01);
(Continued)

(58) Field of Classification Search
CPC ........... C25B 1/02; C25B 3/23; C25B 15/081; C07C 5/02
(Continued)

(56) References Cited

U.S. PATENT DOCUMENTS 3,234,050 A * 2/1966 Beltzer .................. H01M 8/00
204/263
4,620,914 A * 11/1986 Abens ....................... C25B 1/02
205/639
(Continued)

FOREIGN PATENT DOCUMENTS

CA       2875293 A1    12/2013
CN     105200448 B     8/2017

OTHER PUBLICATIONS

An et al., "The Electrochemical Hydrogenation of Edible Oils in a Solid Polymer Electrolyte Reactor. I. Reactor Design and Operation," Journal of the American Oil Chemists' Society (Aug. 1998), vol. 75, No. 8, pp. 917-925. (Year: 1998).*
(Continued)

*Primary Examiner* — Edna Wong
(74) *Attorney, Agent, or Firm* — Oyen Wiggs Green & Mutala LLP

(57) ABSTRACT

Apparatuses and methods for performing coupled chemical and electrochemical reactions are disclosed. An electrochemical cell has a first reaction chamber configured to perform a chemical reaction and an anode chamber configured to perform an electrochemical reaction. The first reaction chamber and the anode chamber are separated by a first membrane. The first membrane acts as a cathode of the cell, a hydrogen-selective layer and a catalyst. The first membrane may comprise a layer of palladium or a palladium alloy. An ion exchange membrane separates the first membrane and the anode chamber. The chemical and electro-
(Continued)

chemical reactions may respectively be hydrogenation and dehydrogenation reactions.

12 Claims, 15 Drawing Sheets

(51) Int. Cl.
| | |
|---|---|
| C07C 5/02 | (2006.01) |
| C07C 5/09 | (2006.01) |
| C25B 9/19 | (2021.01) |
| C25B 15/08 | (2006.01) |
| C25B 13/02 | (2006.01) |
| C25B 13/04 | (2021.01) |

(52) U.S. Cl.
CPC ............. *C25B 13/02* (2013.01); *C25B 13/04* (2013.01); *C25B 15/08* (2013.01); *C07C 2523/44* (2013.01)

(58) Field of Classification Search
USPC .................................. 205/413, 637; 585/257
See application file for complete search history.

(56) References Cited

U.S. PATENT DOCUMENTS

| | | | | |
|---|---|---|---|---|
| 6,218,556 | B1* | 4/2001 | Pintauro | C11C 3/12 205/462 |
| 6,224,741 | B1* | 5/2001 | Yoshida | C10G 45/32 205/633 |
| 6,238,530 | B1 | 5/2001 | Yoshida et al. | |
| 2006/0231415 | A1* | 10/2006 | Christensen | C02F 1/46104 205/688 |
| 2014/0110268 | A1* | 4/2014 | Jackson | C25B 3/25 205/351 |

OTHER PUBLICATIONS

Huang et al., "A Bilateral Electrochemical Hydrogen Pump Reactor for 2-Propanol Dehydrogenation and Phenol Hydrogenation," Green Chemistry (2016), vol. 18, No. 8, pp. 2353-2362. (Year: 2016).*
Sato et al., "Low-Temperature Hydrogenation of Toluene by Electrolysis of Water with Hydrogen Permeable Palladium Membrane Electrode," Chemistry Letters (Apr. 5, 2017), vol. 46, No. 4, pp. 477-480. (Year: 2017).*
Huang, Shiqi et al., "A bilateral electrochemical hydrogen pump reactor for 2-propanol dehydrogenation and phenol hydrogenation", Green Chemistry 18:2353-2362 (2016).
Al-Mufachi, N.A. et al., "Hydrogen selective membranes: A review of palladium-based dense metal membranes", Renewable and Sustainable Energy Reviews 47:540-551 (2015).
Itoh, N. et al., "Selective hydrogenation of phenol to cyclohexanone using palladium-based membranes as catalysts", Applied Catalysis A: General 107:83-100 (1993).
Kurimoto, A. et al., "Deuteration of Alkynes using a Palladium Membrane Reactor", date unknown.
Wicke, E. et al., "Hydrogen in Palladium and Palladium Alloys". In Hydrogen in Metals II; Topics in Applied Physics, Springer, Berlin, Heidelberg, 73-155 (1978).
Lewis, F. A., "The Palladium-Hydrogen System Part III: Alloy Systems and Hydrogen Permeation", Platinum Metals Rev. 26:121-128 (1982).
Shebo, R.S. et al., "Complete electron economy by pairing electrolysis with hydrogenation". Nature Catalysis, 1:501-507 (Jul. 2018).
Shebo, R.S. et al., "Complete electron economy by pairing electrolysis with hydrogenation". Nature Catalysis, 1, supplementary information (Jul. 2018).

Paddon, C.A., et al. "Towards paired and coupled electrode reactions for clean organic microreactor electrosyntheses", J Appl Electrochem 36:617-634 (2006).
Frontana-Uribe, B.A. et al., "Organic electrosynthesis: a promising green methodology in organic chemistry", Green Chemistry 12:2099-2119 (2010).
Iwakura, C. et al., "A New Successive System for Hydrogenation of Styrene Using a Two-Compartment Cell Separated by a Pd Sheet Electrode", Journal of The Electrochemical Society, vol. 143, No. 4 (1996).
Inoue, H. et al., "Successive hydrogenation of styrene at a palladium sheet electrode combined with electrochemical supply of hydrogen", Chemical Communication, Issue 1 (1996).
Iwakura, C. et al., "A new hydrogenation system of 4-methylstyrene using a palladinized palladium sheet electrode", Journal of Electroanalytical Chemistry, vol. 431, Issue 1, 43-45 Jun. 30, 1997.
Iwakura, C. et al., "Successive hydrogenation of styrene using a two-compartment cell separated by Hydrogen storage alloy sheet electrodes", Denki Kagaku (1997).
Inoue, H. et al., "Chemical deposition of Palladium black and its catalytic effect of hydrogenation of 2-octene", Denki Kagaku, 65, No. 12 (1997).
Inoue, H. et al., "Effect of Pd black deposited on successive hydrogenation of 4-methylstyrene with active hydrogen passing through a Pd sheet electrode", Journal of The Electrochemical Society, vol. 145, No. 1 (1998).
Yoshida, Y. et al., "Chemical deposition of foreign metals on a Pd sheet and its application to continuous hydrogenation of 4 methylstyrene", Journal of Electroanalytical Chemistry, vol. 444, issue 2, 203-207 (Mar. 1998).
Iwakura, C. et al., "New hydrogenation systems of unsaturated organic compounds using noble metal-deposited palladium sheet electrodes with three-dimensional structures", Journal of Materials Research, vol. 13, issue 4, 821-824 (Apr. 1998).
Iwakura, C. et al., "Catalytic reduction of carbon dioxide with atomic hydrogen permeating through palladized Pd sheet electrodes", Journal of Electroanalytical Chemistry 459:167-169 (1998).
Yoshida, Y. et al., "Catalytic reduction of nitrous oxide with atomic hydrogen permeating through palladized Pd sheet electrodes", Electrochimica Acta 44:3585 3587 (1999).
Yoshida, Y. et al., "Decoloration of azo dye using atomic hydrogen permeating through a Pt-modified palladized Pd sheet electrode", Electrochimica Acta 45:409-414(1999).
Inoue, H. et al., "Dehydrogenation system of formic acid combined with electrochemical oxidation of atomic hydrogen permeating through a palladinized Pd sheet electrode", Electrochem. Solid State Lett. 2 (2):75-76 (1999).
Inoue, H. et al., "Selectivity control of products in consecutive hydrogenation of diphenyacetylene with chemisorbed hydrogen". Electrochemical and Solid-State Letters, 2 (11): 572-573 (1999).
Iwakura, C. et al., "Construction of a new dehydrogenation system using a two-compartment cell separated by a palladized Pd sheet electrode", Journal of Electroanalytical Chemistry, vol. 463, issue 1, 116-118 (Mar. 1999).
Maki, S. et al., "Selective alkene hydrogenation with atomic hydrogen permeating through a Pd sheet electrode", Synthetic Communications 30(19):3575-3583 (2000).
INoue, H., "Control of product distribution in the hydrogenation of crotonaldehyde, butyraldehyde and crotyl alcohol using the successive hydrogenation system", Electrochemistry-Tokyo 69(9):699-701 (2001).
Maki, S. et al., "Effect of solvent and hydrogen during selective hydrogenation", Tetrahedron Letters 42:8323-8327 (2001).
Iwakura, C. et al., "A new successive hydrogenation system", Chem. Ind. 54 (3):140-150 (2000).
Iwakura, C. et al., "Successive hydrogenation and dechlorination systems using palladized ion exchange membranes", Journal of The Electrochemical Society, 151(1) D1-D5 (2004).
Gutierrez, M. et al., "Hydrogenation of chaicones using hydrogen permeating through a Pd and palladized Pd electrodes", Electrochimica Acta 55:5831-5839 (2010).

(56) References Cited

OTHER PUBLICATIONS

Itoh, N. et al., "Regeneration of Anti-oxidant in Lubrication Oil on Bifunctional Palladium Membrane Electrode", Journal of the Japan Petroleum Institute, 55(3):215-218 (2012).

Sato, T. et al., "Using a hydrogen-permeable palladium membrane electrode to produce hydrogen from water and hydrogenate toluene", International Journal of Hydrogen Energy, vol. 41, issue 12, 5419-5427 (Apr. 6, 2016).

Sato, T. et al., Low-temperature Hydrogenation of Toluene by Electrolysis of Water with Hydrogen Permeable Palladium Membrane Electrode, Chem. Lett. 46:477-480 (2017).

Yan, B. et al., "Mixed Electron-Proton Conductors Enable Spatial Separation of Bond Activation and Charge Transfer in Electrocatalysis", J. Am. Chem. Soc. 141:11115-11122 (2019).

Kanyanee, T. et al., "Indirect (hydrogen-driven) electrodeposition of porous silver onto a palladium membrane", Journal of Solid State Electrochemistry (Apr. 2020).

Sherbo, R.S. et al., "Efficient Electrocatalytic Hydrogenation with a Palladium Membrane Reactor", J. Am. Chem. Soc. 141:7815-7821 (2019).

Delima, R.S. et al., "Supported palladium membrane reactor architecture for electrocatalytic hydrogenation", J. Mater. Chem, a., 7:26586-26595 (2019).

Jansonius, R.P. et al., "Hydrogenation without H2 Using a Palladium Membrane Flow Cell", Cell Reports Physical Science (Jul. 2020).

Kurimoto, A. et al., "Electrolytic deuteration of unsaturated bonds without using D2", Nature Catalysis, 3:719-726 (Sep. 2020).

\* cited by examiner

METHODS AND APPARATUS FOR PERFORMING CHEMICAL AND ELECTROCHEMICAL REACTIONS

CROSS-REFERENCE TO RELATED APPLICATIONS

This application claims benefit from U.S. application No. 62/622,305 filed 26 Jan. 2018. For purposes of the United States, this application claims the benefit under 35 U.S.C. § 119 of U.S. application No. 62/622,305 filed 26 Jan. 2018 and entitled METHOD AND APPARATUS FOR PERFORMING CHEMICAL AND ELECTROCHEMICAL REACTIONS IN TANDEM which is hereby incorporated herein by reference for all purposes.

FIELD

This invention relates generally to apparatuses and methods for performing chemical reactions involving hydrogen. Specific embodiments provide electrochemical cells and methods which apply such cells for the synthesis of organic products for use in various industries such as the pharmaceutical, petrochemical and food industries.

BACKGROUND

Organic electrosynthesis is a potentially cost-effective, scalable and green method for synthesizing organic products. Renewable electricity may be used to drive the synthesis reactions. Most of the organic electrosynthesis transformations described in the literature involve reactions occurring at either the anode or cathode of a cell. In such cases, reactions occurring at the other electrode produce waste products.

Paired electrosynthesis forms useful products at both electrodes. Some known examples have combined gas production or conversion (e.g., hydrogen evolution, carbon dioxide reduction) with an organic transformation or have combined two organic transformations. Prior art electrochemical cells are configured to perform both transformations in the same electrolyte and solvent medium. A major challenge for paired electrolysis is ensuring that the reaction conditions are suitable for both chemical transformations. The scope of feasible reactions performed in prior art electrochemical cells is limited by the compatibility of the reactants and products with each other, as well as the supporting electrolyte and the solvent medium. Some examples of paired electrosynthesis are described in:

Paddon C A, et al. (2006) Towards paired and coupled electrode reactions for clean organic microreactor electrosyntheses. J Appl Electrochem 36:617-634; and Frontana-Uribe B A, et al. (2010) Organic electrosynthesis: a promising green methodology in organic chemistry. Green Chem 12:2099-2119.

Various hydrogenation reactions are commercially important. Common methods for performing hydrogenation reactions use high pressure hydrogen gas. Creating pressurized hydrogen gas requires a lot of energy and is expensive. Another disadvantage of reactions that require hydrogen gas that has been stored and transported under high pressure is that accommodating the required pressure vessels limits suitable locations for performing the reactions.

The inventors have recognised a general need for improved methods and electrochemical cells capable of performing any combination of hydrogenation reaction and dehydrogenation reaction. There is a particular need for such methods and cells which do not require a supply of hydrogen gas.

SUMMARY

This application has a number of aspects. These include, without limitation:
methods for performing paired chemical reactions;
apparatus useful for performing paired chemical reactions.

The paired reactions can include an electrochemical reaction that generates hydrogen ions and a chemical reaction in which atomic hydrogen is a reactant.

One aspect of the present invention provides an electrochemical cell for performing coupled chemical and electrochemical reactions. The electrochemical cell is capable of producing useful products from both reactions. The configuration of the electrochemical cell may allow for a wide range of combinations of chemical and electrochemical reactions to be performed in the same cell. The electrochemical cell may be configured to completely separate solvents for the chemical and electrochemical reactions from one another by a first membrane.

The first membrane may function as all of a cathode of the cell, a hydrogen selective layer and a catalyst. In some embodiments, the first membrane comprises a layer of palladium or a palladium alloy.

In an example embodiment, the electrochemical cell has three chambers: a first reaction chamber, an intermediate chamber and an anode chamber. The first membrane separates the first reaction chamber and the intermediate chamber. An ion exchange membrane separates the intermediate chamber and the anode chamber.

In some embodiments, the electrochemical cell does not comprise an intermediate chamber. In such embodiment, the first membrane and the ion exchange membrane may be touching, separated by a porous separator or separated by a small space.

Other aspects of the invention provide methods for performing coupled chemical and electrochemical reactions. An example of such methods comprises oxidizing at the anode a second reactant to form one or more oxidized products. The oxidization reaction releases one or more hydrogen ions. The hydrogen ions may migrate through the ion exchange membrane towards the first membrane. The hydrogen ions may be reduced to form hydrogen atoms on the first membrane. The hydrogen atoms may then diffuse through the first membrane into a first reaction chamber where they react with a first reactant.

In some embodiments, first and second reactants are organic compounds and form useful organic compounds as products in the chemical and electrochemical reactions. The chemical and electrochemical reactions may, for example, be hydrogenation and dehydrogenation reactions respectively.

In some embodiments, the first reactant is dissolved in a first solvent in the first reaction chamber. The first solvent may, for example, be an aqueous solvent or an organic solvent. In some embodiments, the second reactant is dissolved in a second solvent in the anode chamber. A third solvent may be present in the intermediate chamber. The first, second and third solvents may be the same or different solvents. The second and third solvents may be protic solvents. The protic solvent may comprise an electrolyte.

In some embodiments, the first membrane comprises a layer of catalyst applied on a surface of the hydrogen selective layer. In some embodiments, the first membrane comprises a porous support layer applied on one or both surfaces of the hydrogen selective layer.

Further aspects and example embodiments are illustrated in the accompanying drawings and/or described in the following description.

BRIEF DESCRIPTION OF THE DRAWINGS

The accompanying drawings illustrate non-limiting example embodiments of the invention.

DETAILED DESCRIPTION

Figure 1A:
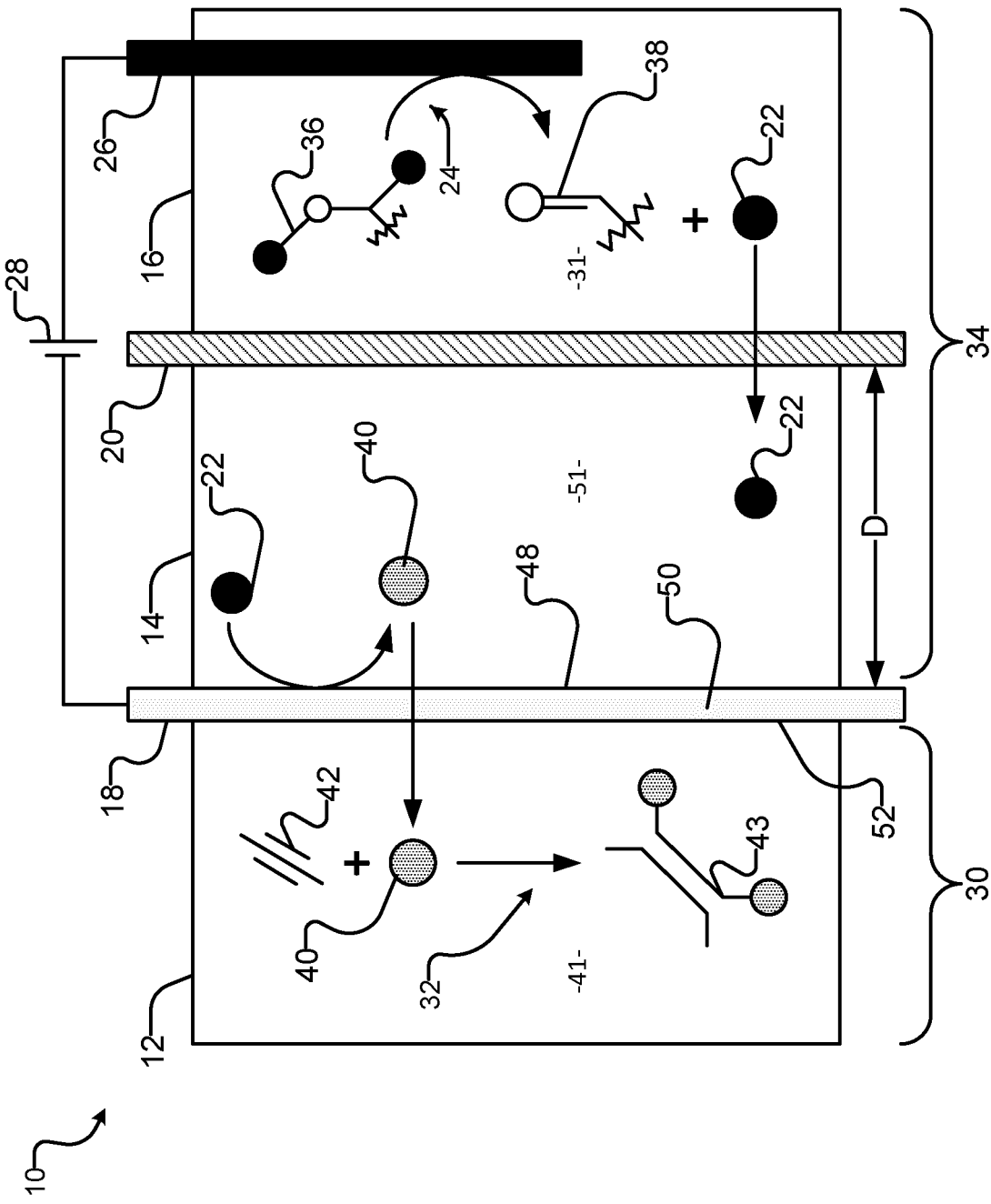
FIG. 1A is a schematic diagram of an electrochemical cell according to an example embodiment of this invention.

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive sense.

An aspect of the invention relates to a cell for performing paired synthesis. A first reaction chamber of the cell is separated from the remainder of the cell by a first membrane that consists of or comprises a dense layer of a material that passes atoms of hydrogen (i.e. any isotope of hydrogen) and blocks other reactants including hydrogen ions. Such a layer may be called "selectively permeable to hydrogen". This layer may be called a "hydrogen selective layer".

In some embodiments the first membrane comprises a dense layer of palladium or a palladium alloy. Here, 'dense' means non-porous such that to pass through the membrane, hydrogen atoms must be absorbed into and pass through the metallic lattice of the layer of palladium or palladium alloy.

In operation, hydrogen ions (e.g. protons) may be produced at an anode in an anode chamber of the cell. These ions may, for example, be produced in a dehydrogenation half-reaction or an oxidation half reaction. The hydrogen ions may migrate to the first membrane, enter the hydrogen selective layer as absorbed hydrogen atoms and pass through the first membrane into the first reaction chamber. Upon reaching the first reaction chamber the hydrogen may participate in a chemical reaction with a reactant in the first reaction chamber. The chemical reaction may, for example, be a reduction reaction, such as a hydrogenation reaction. Ideally the reaction that occurs in the first reaction chamber and an electrochemical reaction that occurs in the anode chamber may each produce one or more desired useful products.

In some embodiments the first membrane serves as two or more of, or all of: 1) a cathode of the cell; 2) a hydrogen-selective layer; 3) a catalyst which helps to promote a desired chemical reaction in the first reaction chamber; and 4) a separator which separates a solvent and reactants in the first reaction chamber from a different solvent or solvents used in other parts of the cell. For example, the first reaction chamber may contain reactants dissolved in a suitable organic solvent while the anode chamber may contain reactants in an aqueous solvent or a protic solvent.

To prevent reactants and/or products of the electrochemical reactions that occur in the anode chamber from participating in further undesired reactions at the first membrane, a second membrane is provided between the first membrane and the anode. The second membrane allows hydrogen ions to pass from the anode chamber to reach the first membrane but blocks other reactants and/or products present in the anode chamber from reaching the first membrane. The second membrane may optionally be spaced apart from the first membrane to define an intermediate chamber. The intermediate chamber may comprise the same or a different solvent than is used in the anode chamber.

In some embodiments one or more additional catalyst materials are provided on the anode and/or on the first membrane.

A suitable current source may be connected to drive an anode-side reaction and to cause ions to migrate to the first membrane by delivering electrons to the cathode and removing electrons from the anode. A chemical reaction in the first reaction chamber may then occur simultaneously with an electrochemical reaction in the anode chamber to produce useful products. Such products may comprise useful organic compounds, for example.

In some embodiments the cell comprises three compartments. An intermediate compartment between the anode compartment and the first reaction compartment may be separated from the anode compartment by an ion permeable second membrane (e.g. a Nafion™ membrane) that allows hydrogen ions to pass from the anode compartment into the intermediate compartment. Once in the intermediate compartment the hydrogen ions can reach the first membrane where they are reduced to hydrogen by a cathodic electrochemical reaction. The hydrogen enters the first membrane (e.g. is absorbed into a dense palladium metal lattice or a lattice of a dense metallic palladium alloy) and travels through the first membrane to the first reaction compartment.

FIG. 1A illustrates an example electrochemical cell 10 that comprises a first reaction chamber 12, an intermediate chamber 14 and an anode chamber 16. A first membrane 18 separates first reaction chamber 12 and intermediate chamber 14. A second membrane 20 separates intermediate chamber 14 and anode chamber 16.

First membrane 18 serves as a cathode. An anode 26 is exposed to anode chamber 16. A power source 28 applies a potential difference between anode 26 and first membrane 18. Power source 28 may be configured to maintain a desired electric current between first membrane 18 and anode 26 and/or to maintain a potential difference between first membrane 18 and anode 26 at a desired level or in a desired range.

First membrane 18 is selectively permeable to hydrogen. First membrane 18 selectively allows absorbed hydrogen atoms 40 to pass through first membrane 18 while first membrane 18 essentially blocks passage of all other ions, electrolytes and solvents. In particular, first membrane 18 may be made of a material which is selectively permeable to absorbed hydrogen atoms 40. Absorbed hydrogen atoms 40 may transition into the bulk of the lattice 50 of first membrane 18, diffuse through lattice 50 and transition to an opposing second surface 52 within first reaction chamber 12. Hydrogen atoms 40 may then react with reactant 42 to yield one or more product compounds 43. In some embodiments the material of first membrane 18 also acts as a catalyst for the hydrogenation reaction 32.

In an example embodiment, first membrane 18 is made up of at least one metal. The metal may, for example, have a crystalline lattice that provides interstitial sites that can accept hydrogen atoms. For example, first membrane 18 may be made from palladium (Pd) metal. Palladium is highly selective for passing hydrogen and is impermeable to most practical solvents and electrolytes. Palladium metal has a face-centered cubic crystal lattice that is capable of hosting hydrogen atoms up to a hydrogen/palladium ratio (H:Pd) of approximately 0.7 ($PdH_{0.7}$). Another example metal that may be used for first membrane 18 is a hydrogen permeable palladium alloy. Examples of palladium alloys that may be used to make first membrane 18, include but are not limited to: Pd—Ag, Pd—Sn, Pd—Au, Pd—Pb, Pd—B, Pd—Pt, Pd—Rh, Pd—Ni and Pd—Cu. Other metals that have high permeability to hydrogen include niobium, vanadium and tantalum.

Second membrane 20 may be an ion exchange membrane. In an example embodiment, second membrane 20 is a membrane that is commercially available under the product name Nafion®.

Protons 22 released from an electrochemical reaction 24 performed in anode chamber 16 migrate through second membrane 20 into intermediate chamber 14. Reaction 24 may comprise an oxidation reaction. In some embodiments, reaction 24 comprises a dehydrogenation reaction.

Anode 26 may comprise platinum metal, for example. Other suitable materials can be used as the anode. For example, metals such as palladium metal and metal oxides such as nickel oxide (NiOx) or ruthenium (IV) oxide ($RuO_2$) may be used for anode 26. Carbonaceous materials such as graphite may also be used for anode 26.

Anode chamber 16 may also comprise an electron transfer mediator. The electron transfer mediator may acts as a catalyst to increase the rate of the reaction in the anode chamber. The electron transfer mediator may be dissolved in solvent 31. In an example embodiment, the electron transfer mediator is TEMPO (2,2,6,6-tetramethyl-1-piperidine N-oxyl).

First reaction chamber 12 comprises a chemical compartment 30 containing a reactant 42 in a suitable solvent 41. Reactant 42 undergoes a chemical reaction with hydrogen 40 which passes through first membrane 18 to yield a product 43. In some embodiments the reaction is a hydrogenation reaction. In some embodiments the reaction takes place between reactant 42 and individual hydrogen atoms which are absorbed in first membrane 18.

In some embodiments, reactant 42 comprises a soluble reducible species. In some embodiments, reactant 42 is a compound comprising an unsaturated bond. In some embodiments, reactant 42 comprises unsaturated organic molecules. Examples of suitable unsaturated organic molecules include, but are not limited to, alkynes, alkenes, aldehydes, ketones, esters, amide, nitro-groups and aromatic rings. In some embodiments, reactant 42 comprises reducible small molecules. Examples of suitable reducible small molecules include, but are not limited to, $CO_2$, CO and $N_2$. In some embodiments, chemical reaction 32 is a hydrogenation reaction.

Chemical compartment 30 may be a flow-through compartment in which solvent 41 containing reactant 42 is circulated through compartment 30 or a batch-type compartment in which solvent 41 containing reactant 42 is initially introduced to compartment 30 and then removed together with reaction product 43 after the reaction has occurred.

Anode chamber 16 and intermediate chamber 14 may be provided by an electrochemical compartment 34 divided by second membrane 20. Anode chamber 16 may be configured to perform an electrochemical reaction 24.

Anode chamber 16 may be a flow-through compartment in which a suitable solvent containing one or more reactants is circulated through anode chamber 16 or a batch-type compartment in which solvent containing one or more reactants is initially introduced to anode chamber 16 and subsequently removed together with one or more reaction products electrochemical reaction 24 has occurred.

In some embodiments, electrochemical reaction 24 is an oxidation reaction, for example a dehydrogenation reaction. In an example embodiment, reaction 24 performed in electrochemical compartment 34 involves oxidizing a reactant 36 to form one or more oxidized products 38. The oxidation reaction releases one or more hydrogen ions 22.

In some embodiments, reactant 36 and one or more oxidized products 38 are organic compounds. In such embodiments, reaction 24 is an oxidation organic reaction. Examples of suitable oxidization organic reaction include, but are not limited to, alcohol oxidation, amine or amide oxidation, carbonyl oxidation, arene functionalization, olefin coupling and olefin oxidation.

Electrochemical reaction 24 is performed in a suitable solvent 31. Any suitable solvent 31 may be used. Solvent 31 may be selected to be compatible with reaction 24. Intermediate chamber 14, when present, may contain a solvent 51 that is the same as or different from solvent 31.

Advantageously, solvent 31 may be different from solvent 41. In some embodiments solvent 41 comprises an organic solvent or a mixture of organic solvents. Suitable organic solvents include but are not limited to, pentane, dichloromethane, methanol, ethanol and acetonitrile. In some embodiments, solvent 41 is an aqueous solvent (e.g. water). In some embodiments solvent 41 comprises or consists of one or more proton-containing solvents such as methanol, ethanol and propanol.

Solvent 31 may be a solvent selected to facilitate electrochemical reaction 24. Foe example, solvent 31 may comprise a protic solvent or an aqueous solvent. Solvent 31 may dissolve one or more suitable electrolytes to provide an electrolyte solution for electrochemical reaction 24. In an example embodiment, intermediate and anode chambers 14, 16 contain electrolytes. Examples of suitable electrolytes include, but are not limited to, acidic electrolytes such as $H_2SO_4$, HCl and $HNO_3$, neutral electrolytes such as $HCO_3$, alkaline (KOH) ion source. Since solvents 31 and 41 can be different, solvent 31 together with any dissolved electrolytes, electron transfer mediator, etc. may be selected to improve the rate and/or selectivity of the specific desired electrochemical reaction 24.

A solvent 31 to be used for performing a particular electrochemical reaction 24 may be selected based at least in part on:
- the solubility of reactant 36 and desired product 38 in the solvent 31;
- the concentration of ions in the solvent 31;
- compatibility of the solvent 31 with the material(s) of anode 26 and any catalysts used to promote electrochemical reaction 24;
- any combination of the above.

Advantageously the reaction conditions in first reaction chamber 12 and anode chamber 16 can be controlled independently. Examples of conditions that can be independently controlled are: choice of reactants, concentrations of reactants, catalysts, choice of solvent, choice of electrolytes or other additives, etc. Although a cell as described herein may be operated at low temperatures (e.g. room temperature) and at low pressures (e.g. atmospheric pressure) it is possible to operate one or both sides of first membrane 18 at pressures above or below atmospheric pressure and/or at temperatures above and/or below room temperature. Within limits imposed by the physical design of first membrane 18 it is possible to independently control temperature and/or pressure on either side of first membrane 18. In some embodiments reactions 24 and/or 32 are performed at temperatures of 100 Celsius or less or 60 Celsius or less or 50 Celsius or less or at about room temperature (e.g. room temperature±15 Celsius).

Furthermore, with the sole exception of hydrogen which can be transported from anode chamber 16 to first reaction chamber 12 through first membrane 18, the reactants, solvent and reaction products in first reaction chamber 12 can be kept isolated from the reactants, solvent and reaction products in anode chamber 16 and so compatibility between the materials present on opposing sides of first membrane 18 is not a problem.

Apparatuses as described above may be applied, for example, to perform any combination of hydrogenation reaction and electrochemical organic oxidation in the same cell.

First membrane 18 (hereinafter referred to collectively by first membrane 18) may have various features of construction. For example, first membrane 18 may optionally comprise:
- surfaces facing toward first reaction chamber 12 and/or intermediate chamber 14 that have morphology that provide high surface areas (e.g. dendrites, roughness, etc.).
- a relatively thin layer of a dense material (e.g. palladium, a palladium alloy etc.) supported on one or both sides by a porous support.
- a separate catalyst for reaction 32 on the side facing first reaction chamber 12. The separate catalyst may be provided on a surface of the hydrogen selective layer and/or on a porous support layer for example.
- any combinations of the above.

First membrane 18 may comprise a self-supporting member made of a hydrogen selective material as described herein. The member may, for example have the form of a sheet, plate, corrugated sheet or plate, casting or the like. However, palladium and other suitable hydrogen selective materials can be expensive and it can be desirable to adopt constructions of membrane 18 which use reduced amounts of such materials.

In an example embodiment, first membrane 18 is provided by a thin dense layer of palladium or another suitable hydrogen selective material on a porous support. The hydrogen selective layer itself may, for example, have a thickness in the range of approximately 1 to 10 µm, about 3 to 8 µm in some cases, or a range of about 1 to 3 µm in some other cases. This construction can reduce the cost of first membrane 18 while providing a dense first membrane 18 that provides a hydrogen permeable physical barrier that separates first reaction chamber 12 from second membrane 20.

Figure 1B:
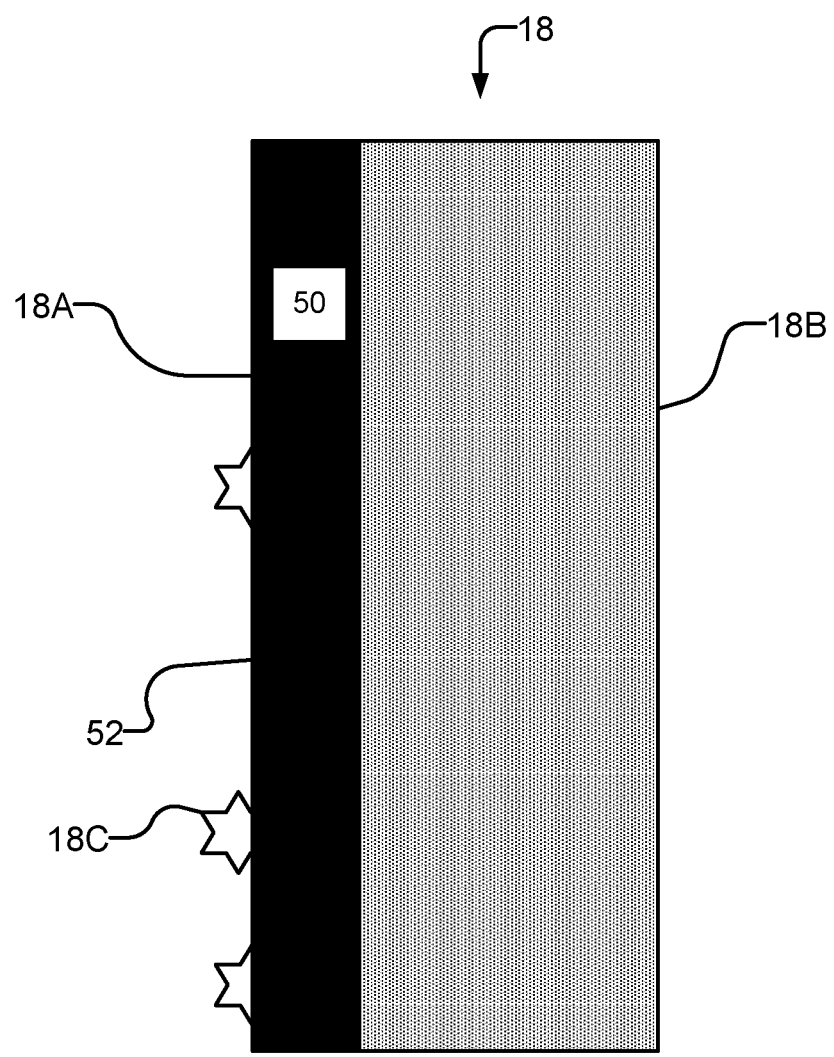
FIG. 1B is a schematic diagram of a first membrane of an electrochemical cell according to an example embodiment of the invention.

FIG. 1B shows an example section of a membrane 18 in which a hydrogen selective layer 18A is on a porous support layer 18B. In this example, support layer 18B is on the side of hydrogen selective layer 18A that faces away from surface 52. Also, in this example, an optional additional catalyst 18C is provided on hydrogen selective layer 18A. In other examples support layer 18B may be on the other side of hydrogen selective layer 18A or hydrogen selective layer 18A may be sandwiched between two porous support layers 18B.

Porous support layer 18B may have pores that are small enough to provide adequate support to hydrogen selective layer 18A and yet are large enough to allow transport of solvent and ions to hydrogen selective layer 18A without excessive reduction in the active surface area of hydrogen selective layer 18A. In general, if hydrogen selective layer 18A is made very thin then porous support layer 18B may need to be selected to have a smaller pore size to provide adequate support for the thin and therefore relatively fragile hydrogen selective layer 18A. In some embodiments, porous support layer 18B has a pore size of in the range of about 0.01 to 1.0 µm. In some embodiments, the pore size of the membrane support is in the range of about 0.05 to 0.1 µm.

Support layer 18B may, for example have a thickness sufficient to provide enough mechanical support to hydrogen selective layer 18A to achieve a desired service life of first membrane 18. The thickness of support layer 18B may, for example, be in the range of about 2 to 200 µm. In some embodiments, the thickness of membrane support is in a range of about 10 to 75 µm.

Support layer 18B may be provided by any suitable substrate. Examples of suitable substrates include, but not limited to, PTFE, anodic aluminum oxide, sintered substrates, and proton conducting membranes such as the commercially available product sold under the name Nafion®.

The dimensions of cell 10 may be adjusted to suit the desired application. Production of desired products may be scaled up, for example by:
- operating plural cells—which may be connected electrically in series and/or in parallel or may have individual power supplies;
- increasing dimensions (e.g. the area of anode 26 and/or membrane 18); and/or
- operating the cell under higher current densities.

The volume of intermediate chamber 14 may be varied. For example, the distance (D) between first membrane 18 and second membrane 20 may be varied. In some embodiments D is small or close to zero. In some embodiments, second membrane 20 is in direct contact with a hydrogen selective layer 18A of first membrane 18 or a porous support layer 18B that supports hydrogen selective layer 18A. In such embodiments intermediate chamber 14 may have a volume that is small or negligible. Some embodiments lack an intermediate chamber 14.

Second membrane 20 may optionally be integrated with first membrane 18. For example, the support layer 18B of FIG. 1B may be provided by second membrane 20.

Figure 1C:
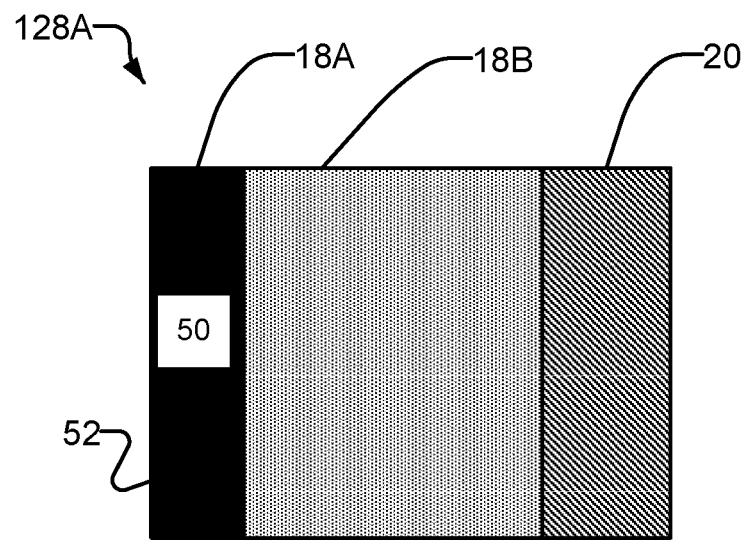
FIGS. 1C and 1D are schematic illustrations of structures that combine first and second membranes.
Figure 1D:
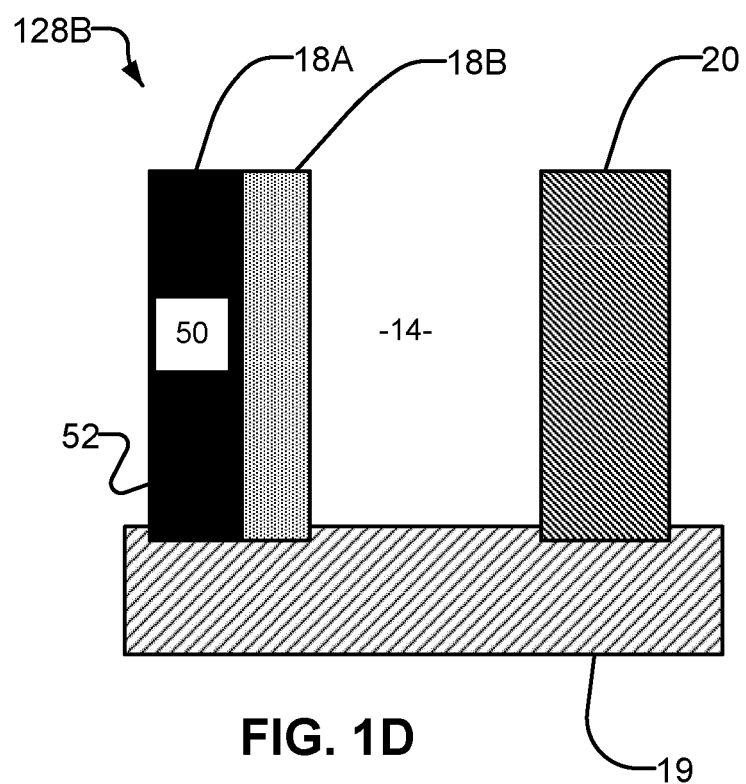

FIGS. 1C and 1D show schematically other example embodiments. FIG. 1C shows an assembly 128A in which second membrane 20 is in direct contact with support layer 18B. A suitable solvent may be supplied to support layer 18B to facilitate passage of hydrogen ions to hydrogen selective layer 18A and/or to assist in hydration of second membrane 20.

FIG. 1D shows an assembly 128B in which second membrane 20 is held spaced apart from support layer 18B by a frame 19 to define an intermediate layer 14. A suitable solvent may be present in intermediate chamber 14 to facilitate passage of hydrogen ions to hydrogen selective layer 18A and/or to assist in hydration of second membrane 20.

In some embodiments first membrane 18 is formed by electrodepositing one or more layers of palladium on one or both sides of a palladium foil. The density of the palladium foil is about 11.9 g/cm$^3$. In some embodiments, the electrodeposited layer of palladium is applied on second surface 52 of first membrane 18. Without being bound to any particular theory, the electrodeposited palladium provides increased surface area which can increase the rate of reaction 32.

Any suitable method for electrodepositing palladium on a palladium foil or other dense hydrogen selective material may be used. In an example embodiment, an Ag/AgCl electrode is used as a reference electrode and a Pt mesh electrode is used as the counter electrode. The electrodeposition is performed in an acidic $PdCl_2$ solution. For example the solution may comprise 15.9 mM $PdCl_2$ dissolved in 1M HCl. Roughly −0.2 V vs. Ag/AgCl potential is applied to the electrodes. The electrodeposition is complete when a charge of about 9 C has passed in the circuit (or after a passage of about 7.38 C/cm$^2$). It may be possible to deposit a dense layer of palladium or another suitable hydrogen selective metal directly on a substrate by electrodeposition, electroless deposition or physical vapour deposition.

In some embodiments, a layer of catalyst (not shown) is applied on second surface 52 of first membrane 18 to promote reaction 32 in first reaction chamber 12. The layer of catalyst may be porous. The catalyst may be heterogenous. Examples of additional catalysts that could be provided to promote hydrogenation reactions include but are not limited to Fe, Pt, Ir, RuI, Rh and Ni.

Figure 2:
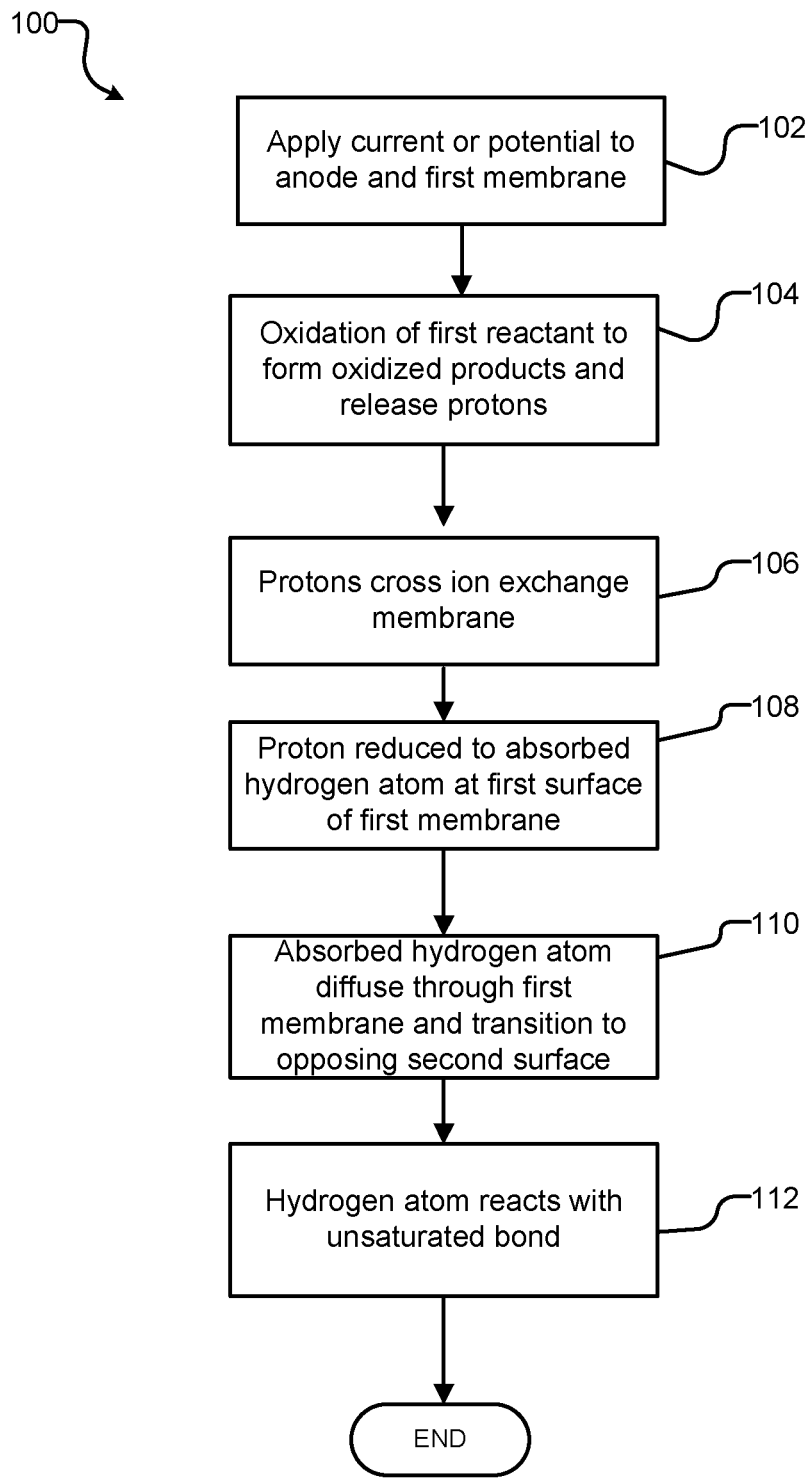
FIG. 2 is a flow chart showing steps in a method for performing coupled reduction and oxidation reactions using the FIG. 1 electrochemical cell according to an example embodiment of the invention.

An aspect of the invention relates to methods for performing paired reactions. The methods may apply a cell of the general type described above. FIG. 2 illustrates an example method 100. In block 102, an electrical current and/or potential is applied between an anode and a first membrane which acts as a cathode. In block 104, a first reactant is oxidized to form one or more oxidized products by an electrochemical reaction at the anode. This results in the release of one or more hydrogen ions (e.g. protons) in an anode chamber housing the anode. In block 106, the hydrogen ions cross an ion exchange membrane from the anode chamber towards first membrane. In block 108, the hydrogen ions are reduced to absorbed hydrogen atoms at a first surface of the first membrane. In block 110, the absorbed hydrogen atoms transition into the bulk of the lattice of the first membrane, diffuse through first membrane and are transported to an opposing second surface of the first membrane positioned within a reaction chamber. In block 112, the hydrogen atoms react with a second reactant dissolved in solvent within the reaction chamber to form a hydrogenated compound.

Method 100 may be tuned to optimize one or more of product selectivity, current efficiency and reaction rate of each of the paired reactions by adjusting one or more of:
- the applied current, and/or
- the applied electrical potential, and/or
- the type of solvent and electrolyte in the area where each reaction takes place, and/or
- the properties of the first membrane such as the particular metal or metals used to make the membrane hydrogen selective and its surface area, density and thickness, and/or
- concentrations of the reactants, and/or
- temperature, and/or
- pressure, and/or
- additional catalysts present and/or
- any combination of two or more of the above.

Since the starting materials and the desired products for each reaction are different, at least some of these factors may be separately optimized for each of the paired reactions to achieve two high-yielding selective reactions.

In summary, one example aspect of the invention provides a method for performing coupled chemical and electrochemical reactions, the method comprises:
(a) Providing a multichamber electrochemical cell, comprising:
  a. A first chamber for performing a chemical reaction, the first chamber containing a solvent and a soluble reducible species;
  b. Optionally, a second chamber containing a proton-containing electrolyte,
  c. A third chamber for performing an electrochemical reaction, the third chamber containing a proton-containing electrolyte and an oxidizable organic compound dissolved therein, the electrolyte being in contact with an electrode positioned in said chamber
  d. A hydrogen selective (e.g. palladium) electrode positioned between the first chamber and the third chamber; and
  e. An ion conductive membrane positioned between the hydrogen selective electrode and the third chamber;
  f. An electrode positioned within the third chamber; and
(b) Applying an electrical potential or current between the two electrodes such that
  a. The oxidizable organic compound is electrochemically oxidized in the third chamber to produce hydrogen ions and an oxidized product;
  b. The hydrogen ions migrate across the ion exchange membrane to the second chamber where they are reduced to hydrogen atoms by the palladium electrode;
  c. The hydrogen atoms permeate the palladium electrode and react with the soluble reducible species in the first chamber to produce a reduced product.

Another example aspect of the invention provides a multichamber electrochemical cell useful for performing coupled chemical and electrochemical reactions. The cell comprises:
(a) A first chamber for performing a chemical reaction, containing a solvent and a soluble reducible species;
(b) A second (optional) chamber containing an electrolyte;
(c) A third chamber for performing an electrochemical reaction containing
  a. an electrolyte;
  b. an oxidizable organic compound;
  c. an anode immersed in the electrolyte;
(d) A hydrogen selective (e.g. palladium) electrode positioned between the first chamber and the third chamber;
(e) An ion conductive membrane positioned between the hydrogen selective electrode and the third chamber; and
(f) A means (e.g. a power supply, electrical current source, generator, battery, or the like) for applying an electrical potential and/or current between the two electrodes.

The invention is further described with reference to the following specific examples, which are not meant to limit the invention, but rather to further illustrate it.

EXAMPLES

An electrochemical cell of the type illustrated in FIG. 1 and the method of performing paired electrolysis illustrated in FIG. 2 were used to convert 1-hexyne to 1-hexene in chemical compartment 30, and to convert 4-methoxybenzyl alcohol (anisyl alcohol) to 4-methoxybenzaldehyde (anisaldehyde) in electrochemical compartments 34. In the example embodiment, first membrane 18 which separates the chemical and electrochemical compartments is a palladium membrane.

Example 1—Palladium Membrane Properties

Figure 3B:
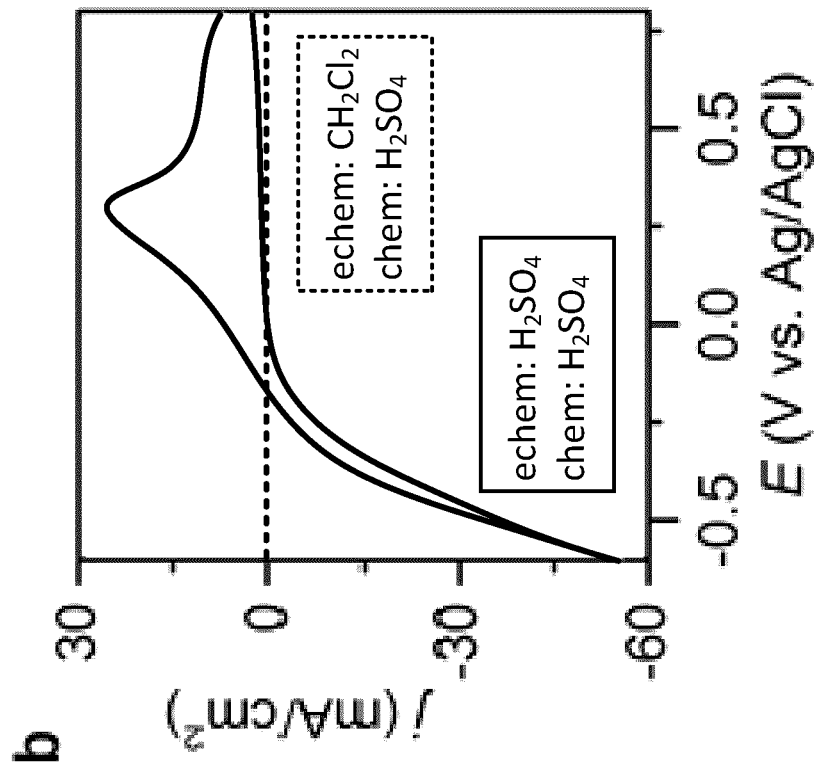
FIG. 3B is a graph depicting CV measurements, with 1 M $H_2SO_4$ in the chemical compartment and a comparison between 0.1 M $TBAPF_6$ in $CH_2Cl_2$ and 1 M $H_2SO_4$ electrolyte in the electrochemical compartments. In these experiments, Pd foil was used as the working electrode, Pt mesh as the counter electrode and Ag/AgCl as the reference electrode.
Figure 3A:
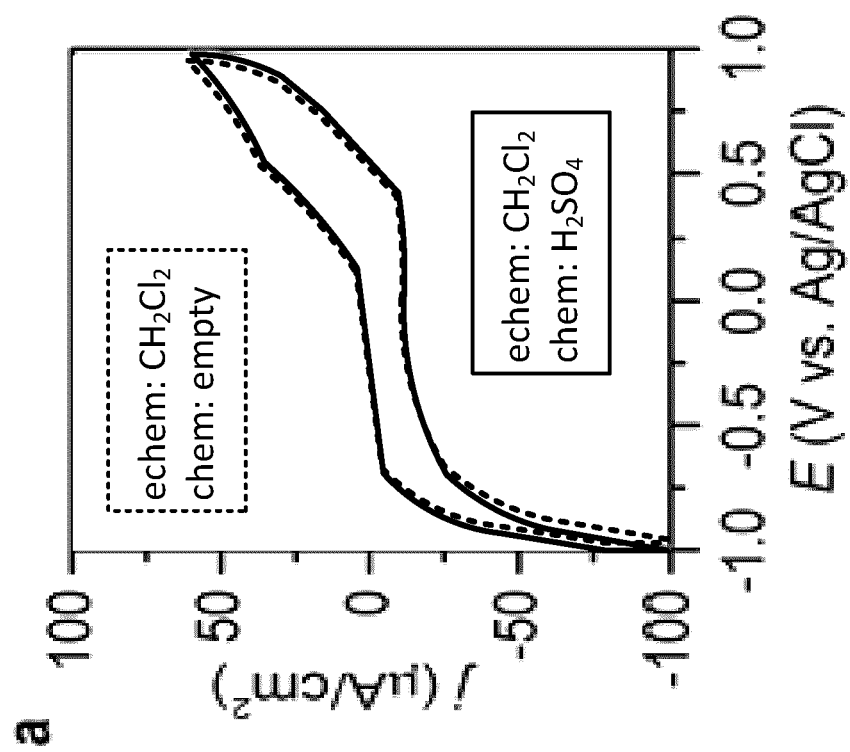
FIG. 3A a graph depicting cyclic voltammogram (CV) measurements, comparing an empty chemical compartment and one with 1 M $H_2SO_4$ when 0.1 M $TBAPF_6$ in $CH_2Cl_2$ is used as the electrolyte in the electrochemical compartments.

FIG. 3A is a graph illustrating cyclic voltammogram measurements of various reaction conditions in the electrochemical compartment to demonstrate the isolation of chemical compartment 30 from electrochemical compartments 34. The electrochemical compartments 34 of the cell were filled with 0.1 M $TBAPF_6$ in $CH_2Cl_2$ electrolyte. Chemical compartment 30 was left empty and opened to air. FIG. 3 shows that the current response (dotted lines) is in the $\mu A\ cm^{-2}$ range, which is consistent with the wide electrochemical window of the $CH_2Cl_2$ electrolyte. Chemical compartment 30 was then charged with 1 M $H_2SO_4$. FIG. 3 shows that the cyclic voltammogram with 1 M $H_2SO_4$ in chemical compartment 30 (solid line) overlaps almost completely with the cyclic voltammogram for the case where chemical compartment 30 was empty. No water electrolysis was visible in the wide electrochemical window. This suggests that no electrochemical reaction was taking place in the chemical compartment of the cell.

When the electrolyte in the electrochemical compartment 34 is replaced with 1 M $H_2SO_4$, the expected response (water electrolysis and palladium absorption and desorption) is observed, as shown in FIG. 3B. This data suggests that the electrochemical cell as shown in FIG. 1 is capable of uncoupling the reaction conditions in the chemical and electrochemical compartments.

Figure 4A:
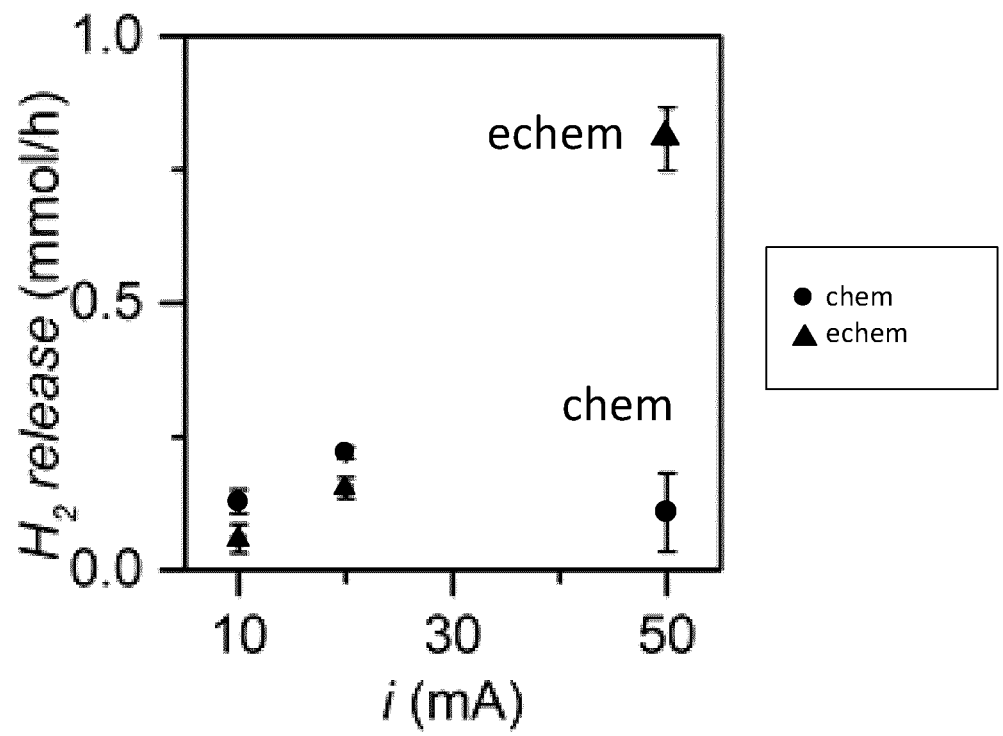
FIG. 4A is a graph showing gas chromatography (GC) measurements of hydrogen evolution from the chemical and electrochemical compartments plotted against various applied currents with 1 M $H_2SO_4$ as the solvent in both compartments.
Figure 4B:
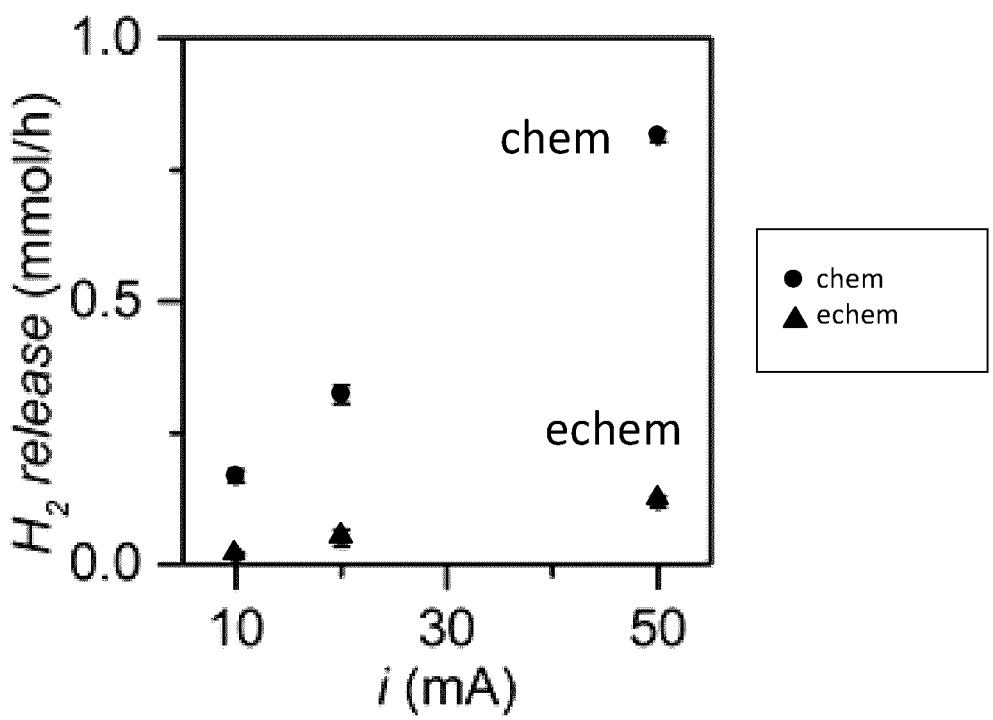
FIG. 4B is a graph showing GC measurements of hydrogen evolution from the chemical and electrochemical compartments plotted against various applied currents with pentane as the solvent in the chemical compartment and 1 M $H_2SO_4$ as the solvent in the electrochemical compartment.

FIGS. 4A and 4B are graphs showing gas chromatography (GC) measurements of hydrogen evolution plotted against applied current. GC measurements were performed to investigate the proportion of hydrogen that could be funneled to the chemical side of the palladium foil which provided first membrane 18 in this experiment. This was performed to demonstrate the feasibility of conducting a hydrogenation reaction in chemical compartment 30. The competition of hydrogen evolution with hydrogenation is of concern because in the configuration of the FIG. 1 electrochemical cell, hydrogen release could occur on either the electrochemical or chemical side of the palladium foil.

Both compartments of the cell were fitted with tubing and the hydrogen gas released was quantified by integration of GC signals. A constant current was applied to the palladium foil and hydrogen evolution was brought to equilibrium at the beginning of the experiment after hydrogen absorption had equilibrated in the foil as well as between each measurement. FIG. 4A shows the rate of hydrogen release (mmol/h) when 1 M $H_2SO_4$ was used as a solvent/electrolyte on both sides of the foil.

Referring to FIG. 4A, at 10 mA and 25 mA applied currents, more hydrogen was released on the side of the foil in chemical compartment 30 than the side of the foil facing electrochemical compartments 34. At 50 mA applied current, 90% of the hydrogen was released on the electrochemical side of the cell.

The experiment was then modified by replacing the 1 M $H_2SO_4$ with pentane in chemical compartment 30. Pentane is a solvent that can be used for 1-hexyne hydrogenation. Referring to FIG. 4B, the majority of the hydrogen formed at all current densities was released on the side of the palladium foil in chemical compartment 30. 90% of the hydrogen was detected on the side of the foil facing chemical compartment 30 at 50 mA applied current. This result was opposite to the results found in the experiment that used 1 M $H_2SO_4$ as the electrolyte. These results indicate that the kinetics of hydrogen movement in this system are dependent on either the rate of recombination of hydrogen or the rate of transition of bulk absorbed hydrogen to adsorbed hydrogen at the side of the foil facing chemical compartment 30. Pentane is a non-coordinating solvent that would not occupy palladium surface sites and would not block the transition of bulk to surface hydrogen or hydrogen recombination. The fact that hydrogen movement can be controlled by adjusting kinetics on the chemical side of the cell suggests that hydrogenation will take place on the chemical side of the palladium foil if the reaction rate is sufficient.

Example 2—Catalytic Hydrogenation Reaction

The hydrogenation of 1-hexyne in pentane in the chemical compartment was then tested in tandem with an oxygen evolution reaction (OER) at the anode having 1 M $H_2SO_4$ as the electrolyte in the electrochemical compartment 34. Aliquots of the reaction mixture were taken every two hours and analyzed by gas chromatography-mass spectrometry (GC-MS). This reaction was performed without the alcohol oxidation to verify that the diffusion of hydrogen atoms through the palladium foil could be leveraged to perform useful organic chemistry.

Figure 5:
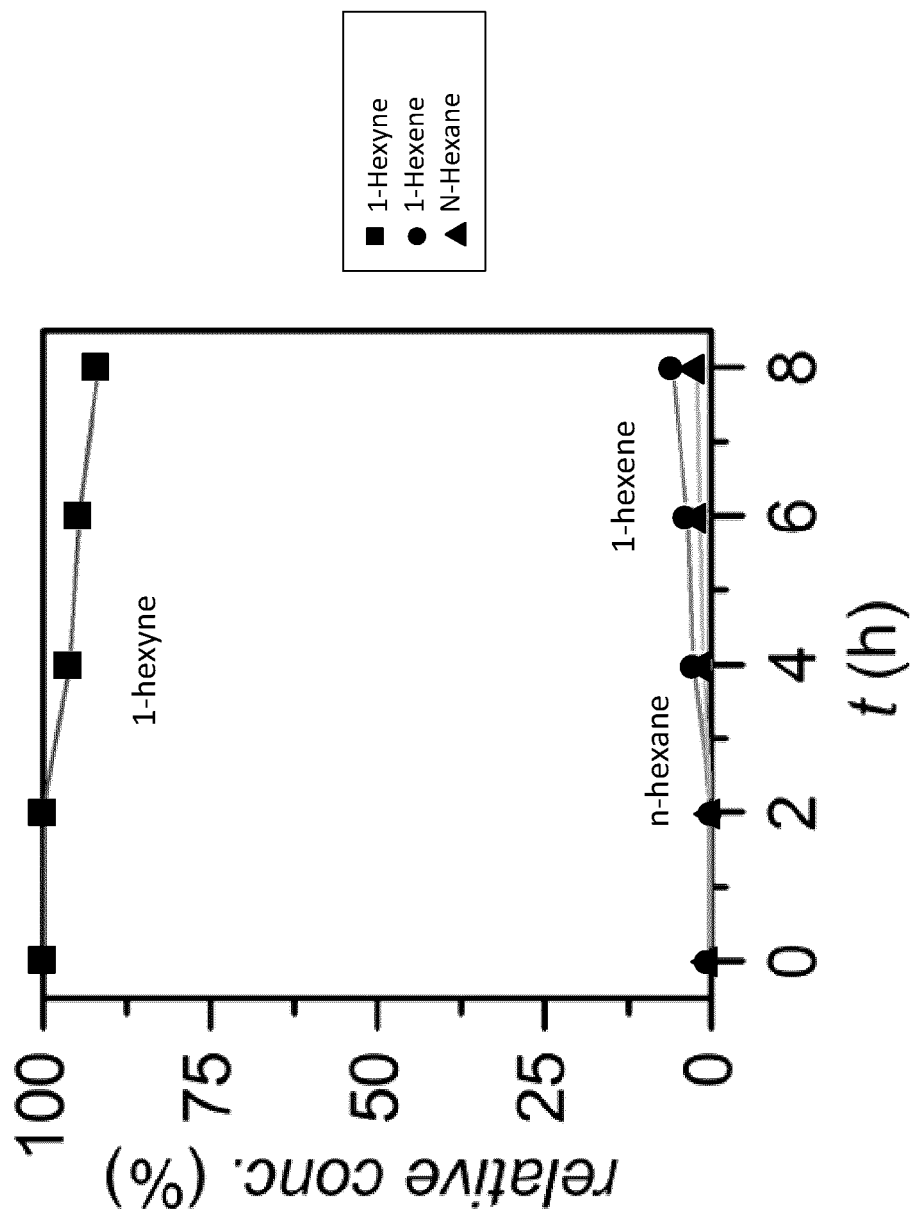
FIG. 5 is a graph showing the relative concentrations of each of 1-hexyne, 1-hexene and n-hexane during a hydrogenation reaction of 1-hexyne dissolved in pentane over the course of an 8 hour experiment without electrodeposited palladium catalyst on the palladium foil.

FIG. 5 is a graph showing the relative concentrations of each of 1-hexyne, 1-hexene, and n-hexane plotted against the duration of the experiment. The results show that the rates of the hydrogenation reaction are slow. Only 6% of the starting material was converted to 1-hexene and 2% to n-hexane (the over-reduction product) after 8 hours of continuous reaction. These data suggested that the palladium foil used I this experiment acts effectively as a membrane but did not show good catalytic ability for hydrogenation. The inventors hypothesized that the slow reaction rates for hydrogenation were a result of the low surface area of the planar palladium foil used in that experiment.

Figure 6A:
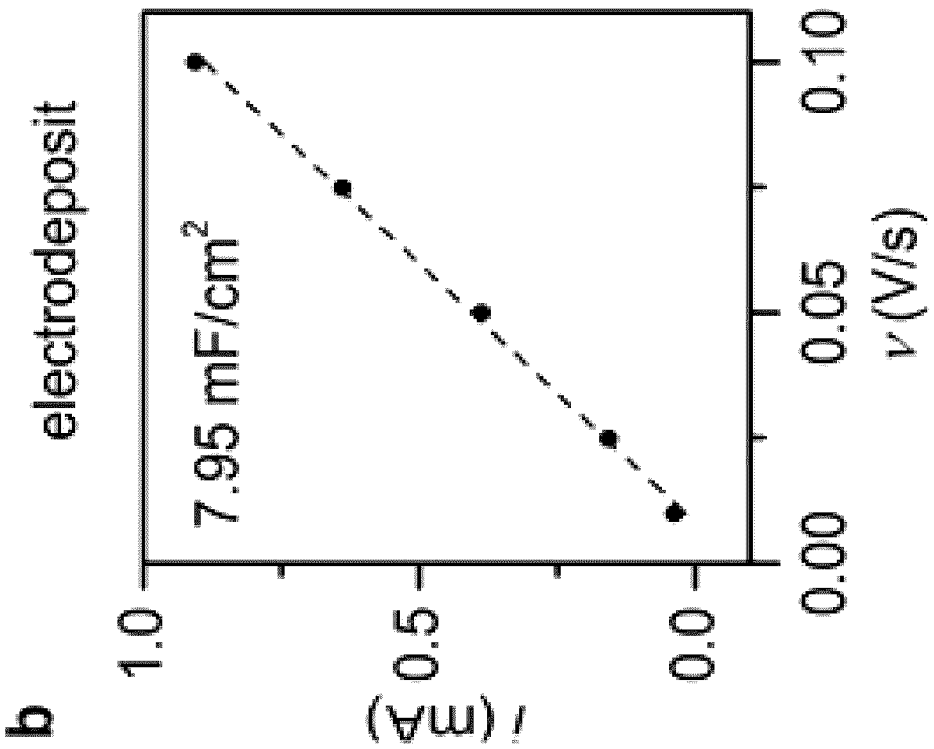
FIG. 6A is a graph illustrating double-layer capacitance electrochemical surface area measurements of a palladium foil membrane.
Figure 6B:
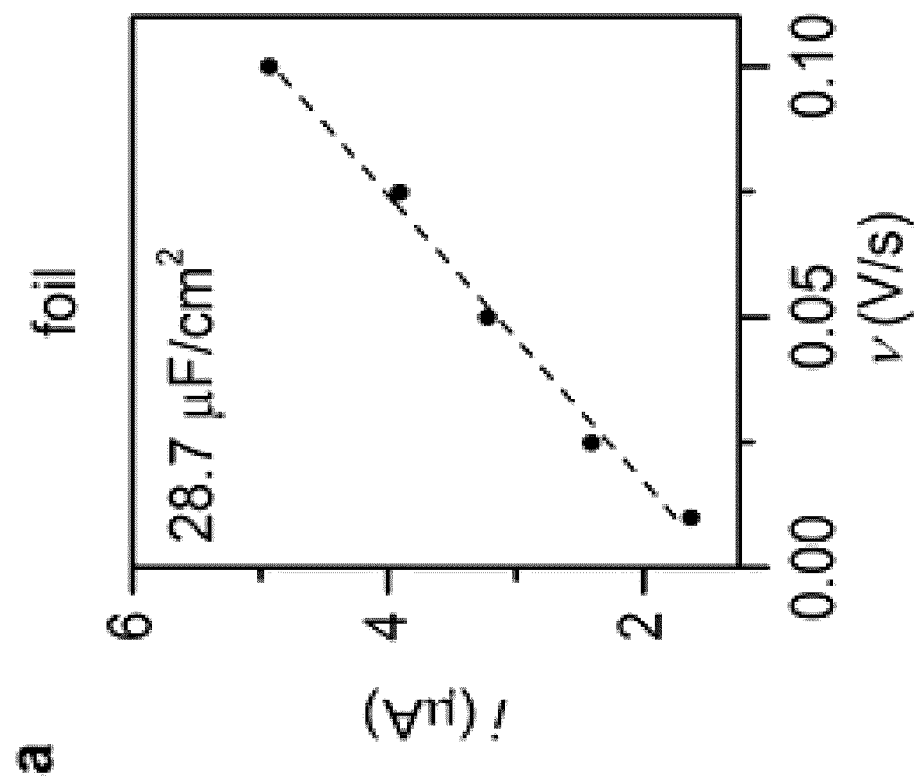
FIG. 6B is a graph illustrating double-layer capacitance electrochemical surface area measurements of electrodeposited palladium.

An additional layer of palladium was then electrodeposited on the palladium foil surface in order to improve the catalytic surface area and the reaction rate of hydrogenation. The electrodeposition was performed in a $PdCl_2$ solution in the presence of 1 M HCl. FIG. 6A is a graph showing double-layer capacitance electrochemical surface area measurements of the palladium foil membrane. FIG. 6B is a graph showing the double-layer capacitance electrochemical surface area measurements of the electrodeposited palladium. Referring to FIGS. 6A and 6B, the surface area of the electrodeposited palladium was increased by a factor of 277, or about 60 times compared to the original palanar palladium foil membrane.

Figure 7A:
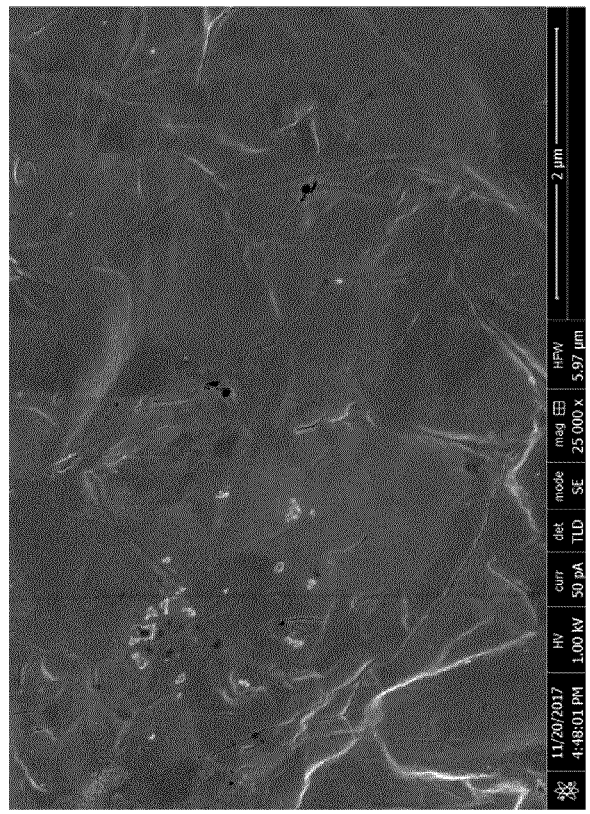
FIG. 7A is a scanning electron microscope (SEM) image of a palladium foil membrane.
Figure 7B:
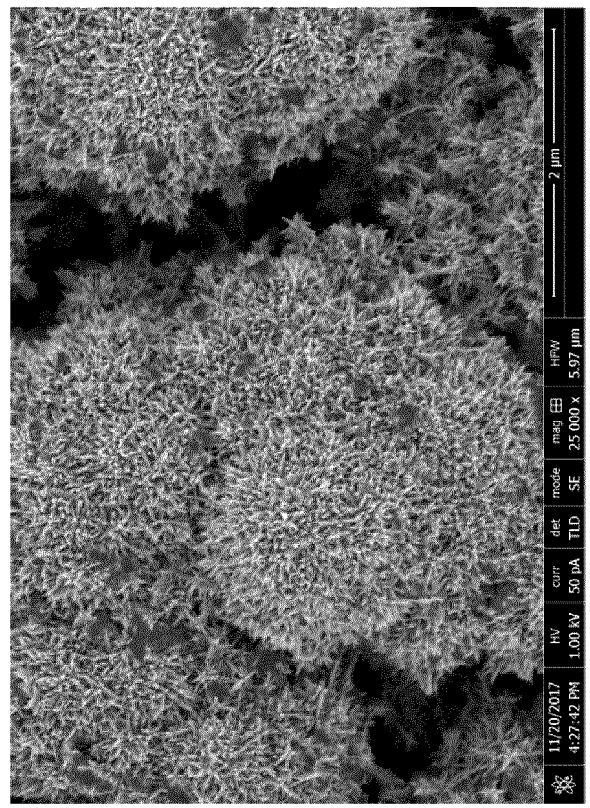
FIG. 7B is a SEM image of electrodeposited palladium on the chemical side of the palladium foil membrane of FIG. 7A.

FIG. 7A is a scanning electron microscope (SEM) image of the palladium foil membrane. FIG. 7B is a SEM image of the electrodeposited palladium on the chemical side of the palladium foil membrane. A comparison of the SEM images of the foil with and without the electrodeposited palladium highlight the significant difference in morphologies between the surfaces of the palladium foil membrane and the electrodeposited palladium. The surface of the electrodeposited palladium comprises a large number of fine projections such as dendrites, whiskers or needles that have a combined surface area much larger than that of the generally smooth surface that was present prior to the electrodeposition (FIG. 7A).

Figure 8:
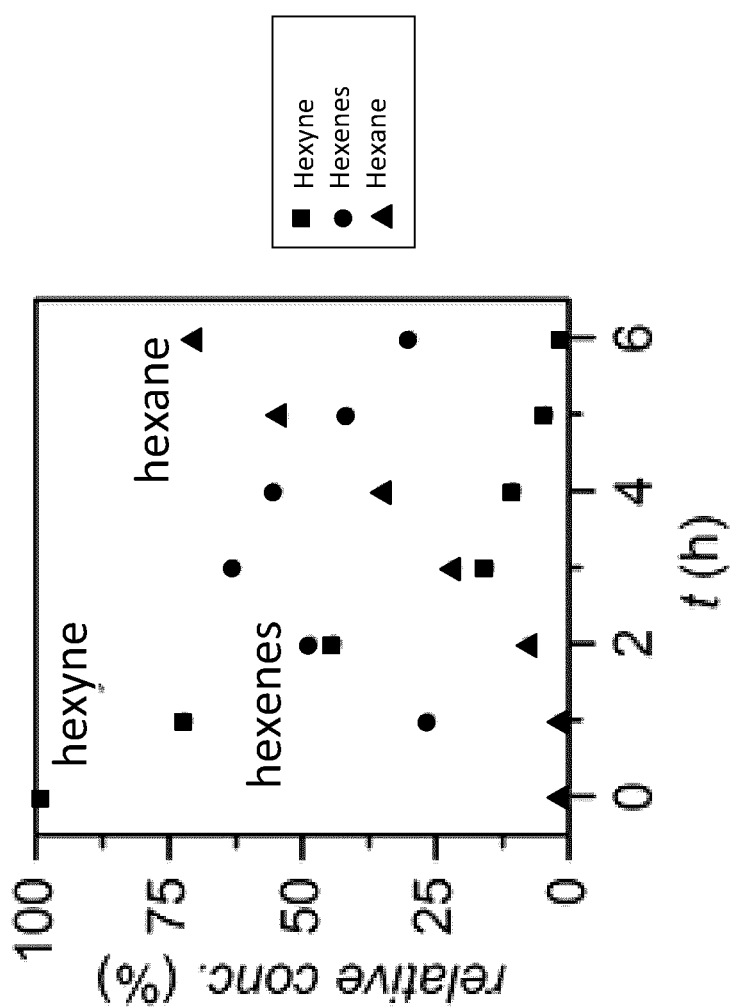
FIG. 8 is a graph showing the relative concentrations of each of 1-hexyne, 1-hexyne, hexenes isomers and n-hexane during the hydrogenation reaction of 1-hexyne over the course of a 6 hour experiment with a layer of palladium electrodeposited on the chemical side of the palladium foil.

1-hexyne hydrogenation was then repeated with the electrodeposited palladium on the chemical side of the foil. FIG. 8 is a graph showing the relative concentrations of 1-hexyne, hexenes isomers and n-hexane after 6 hours of reaction. Referring to FIG. 8, complete consumption of 1-hexyne was found after 6 hours. The hydrogenation of 1-hexyne using the membrane coated with electrodeposited palladium thus accelerates the rate of the reaction significantly.

Example 3—Paired Electrolysis

A paired electrolysis reaction was tested by adding anisyl alcohol dissolved in 1 M $KHCO_3$ containing a redox mediator to anode compartment 16 and 1 M $KHCO_3$ in intermediate chamber 14. 0.1 M 1-hexyne dissolved in pentane was added to first reaction chamber 14 (chemical compartment 30). The anode and cathode sides of electrochemical compartment 34 were separated by a Nafion™ membrane. The reaction was run with an applied current of 50 mA for 5 hours and sample aliquots of both reactions were taken every hour. The hydrogenation reaction was characterized by GC-MS while the alcohol oxidation was characterized by NMR spectroscopy.

Figure 9A:
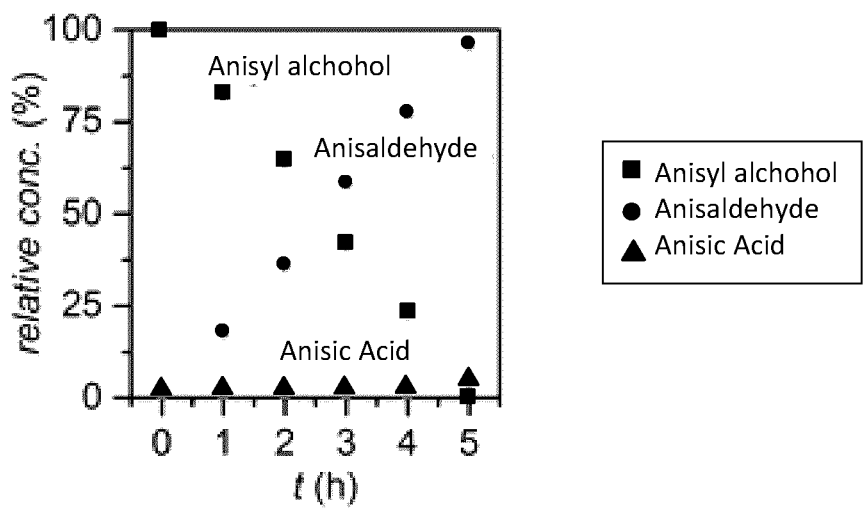
FIG. 9A is a graph showing the relative concentrations of each of anisyl alcohol, anisaldehyde and anisic acid during the alcohol oxidation reaction of anisyl alcohol at an applied current of 50 mA over the course of a 5 hour experiment.
Figure 9B:
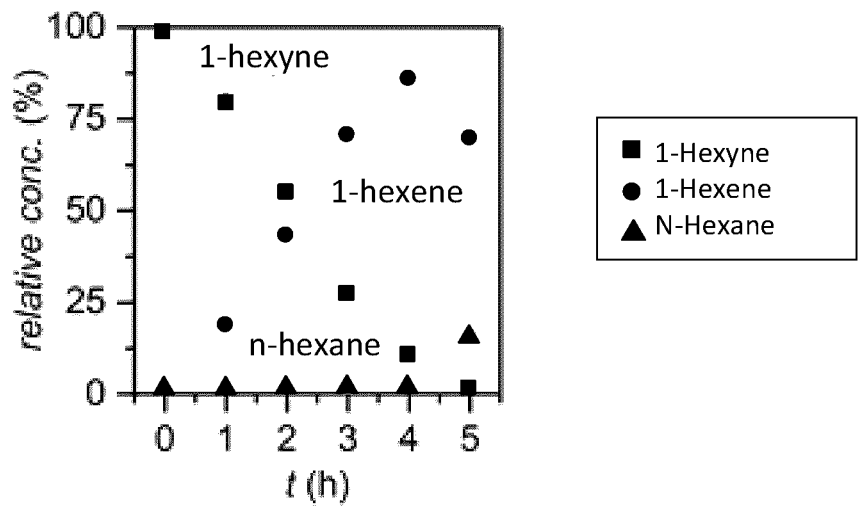
FIG. 9B is a graph showing the relative concentrations of each of 1-hexyne, 1-hexene, and n-hexane during the hydro-genation reaction of 1-hexyne at an applied current of 50 mA over the course of a 5 hour experiment.

Referring to FIGS. 9A and 9B, all starting materials in both reactions were consumed within 5 hours of continuous electrolysis. Both the hydrogenation and oxidation reactions can over-react to form undesired products. Specifically, 1-hexene can further hydrogenate to n-hexane or can isomerize at the palladium surface to (E)- and (Z)-3-hexene, while anisaldehyde can be further oxidized to 4-methoxybenzoic acid (anisic acid).

FIG. 9A shows the progress of the alcohol oxidation. Referring to FIG. 9A, after 5 hours, the reaction produced the desired anisaldehyde product in 96% yield with only 4% of the solution containing anisic acid.

FIG. 9B shows the reaction progress of the hydrogenation reaction. Referring to FIG. 9B, 1-hexene concentration reached a maximum at 4 hours into the reaction, with 86% conversion. At 5 hours, all 1-hexyne has been converted but some 1-hexene has been further hydrogenated to n-hexane. Each of the hydrogenation and oxidation reaction exhibits good selectivity (86-97% desired product) and full conversion after 5 hours.

Figure 9C:
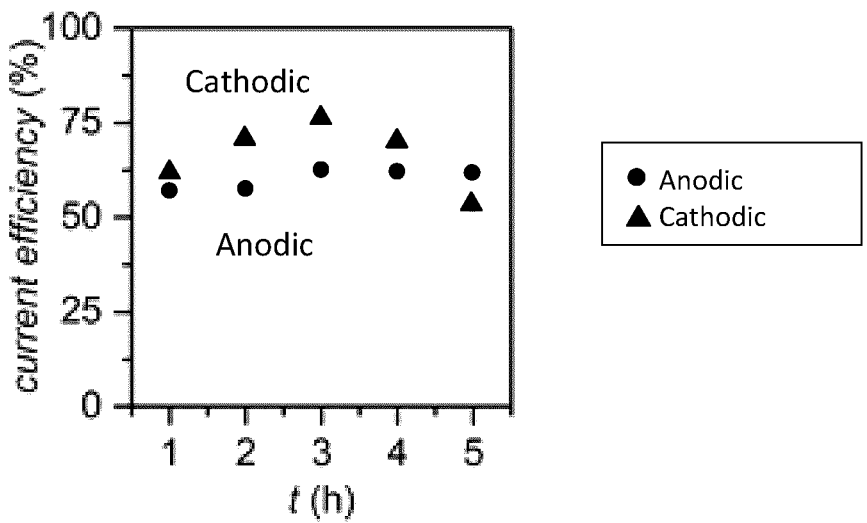
FIG. 9C is a graph showing the current efficiencies for both the anodic and cathodic reactions. A pentane solvent and 1M $KHCO_3$ electrolyte were used along with a Pt anode and an Ag/AgCl reference electrode.

FIG. 9C shows the current efficiencies for the desired product for both the anodic and cathodic reactions. Referring to FIG. 9C, the current efficiency for the hydrogenation reaction were measured to be 60-80%, generally greater than the anodic current efficiencies that were consistently measured to be about 60%.

Figure 10A:
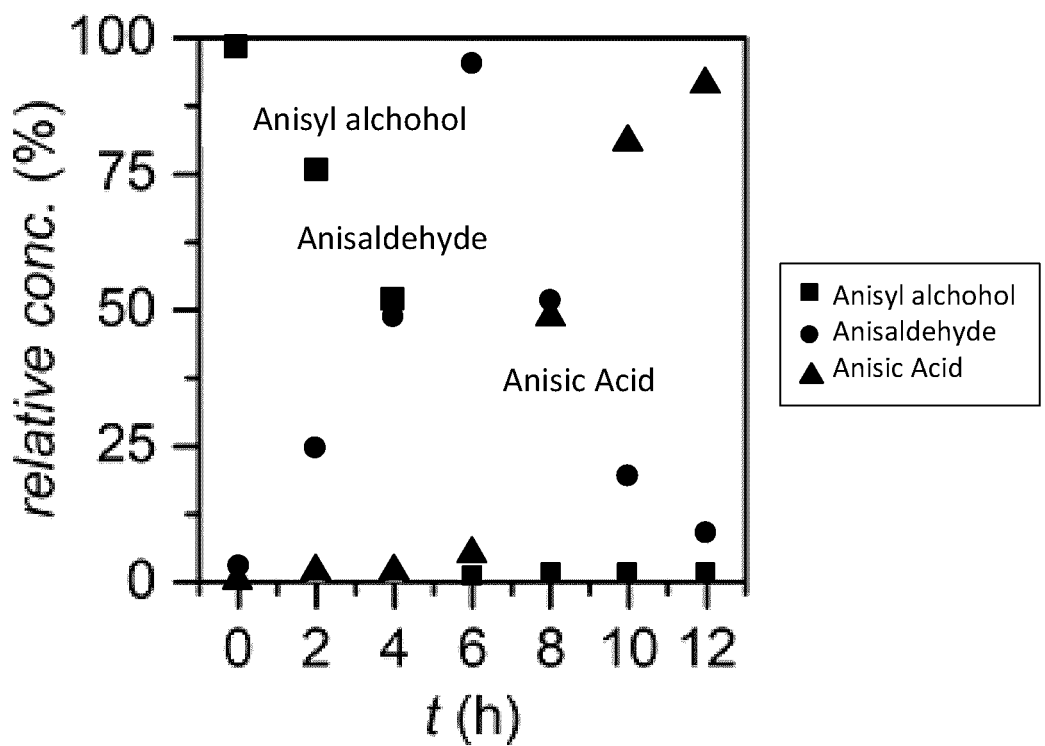
FIG. 10A is a graph showing the relative concentrations of each of anisyl alcohol, anisaldehyde and anisic acid during the alcohol oxidation reaction of anisyl alcohol at an applied current of 25 mA over the course of 12 hour.
Figure 10B:
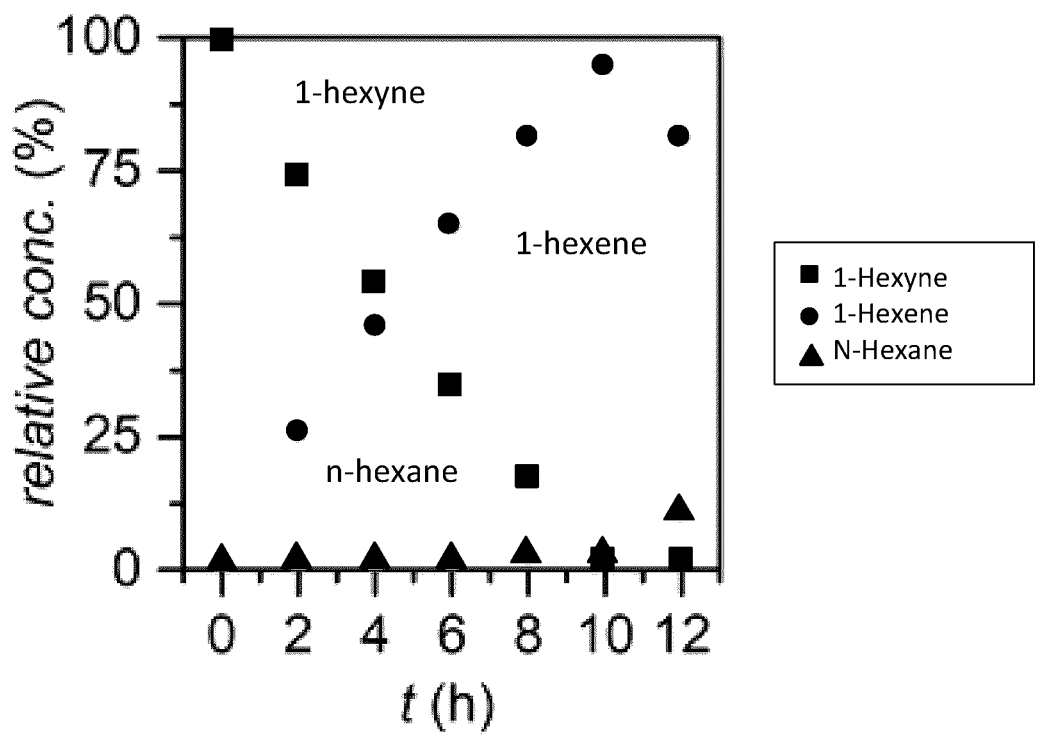
FIG. 10B is a graph showing the relative concentrations of each of 1-hexyne, 1-hexyne, hexenes isomers and n-hexane during the hydrogenation reaction of 1-hexyne over the course of 12 hours at an applied current of 25 mA. A pentane solvent and 1 M $KHCO_3$ electrolyte were used along with a Pt anode and an Ag/AgCl reference electrode.
Figure 11A:
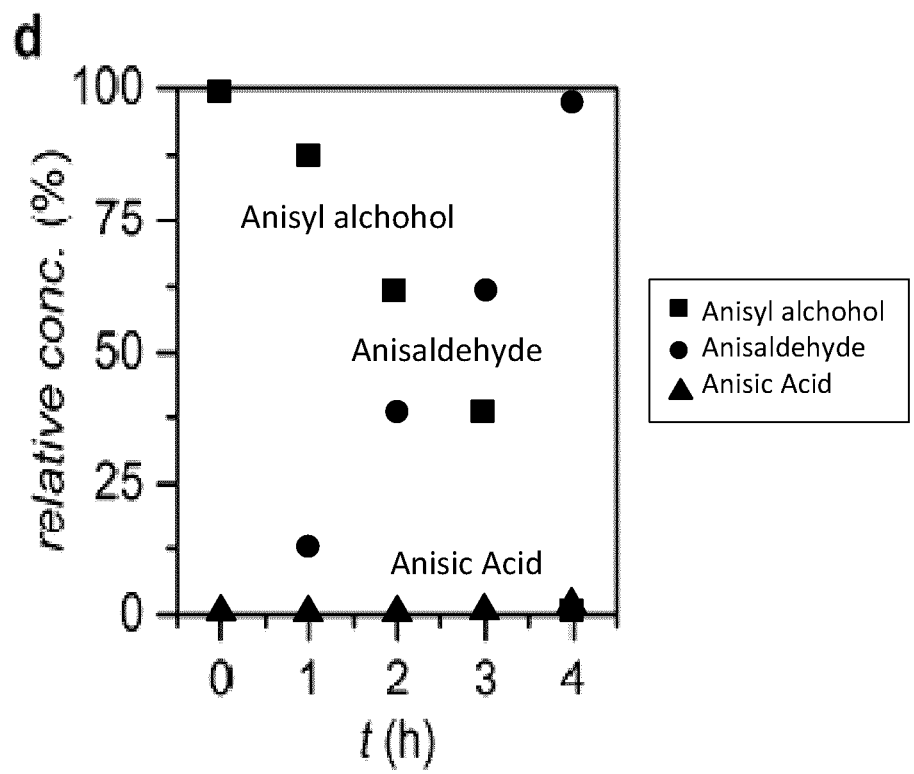
FIG. 11A is a graph showing the relative concentrations of each of anisyl alcohol, anisaldehyde and anisic acid during the alcohol oxidation reaction of anisyl alcohol at an applied current of 75 mA over the course of 4 hours.
Figure 11B:
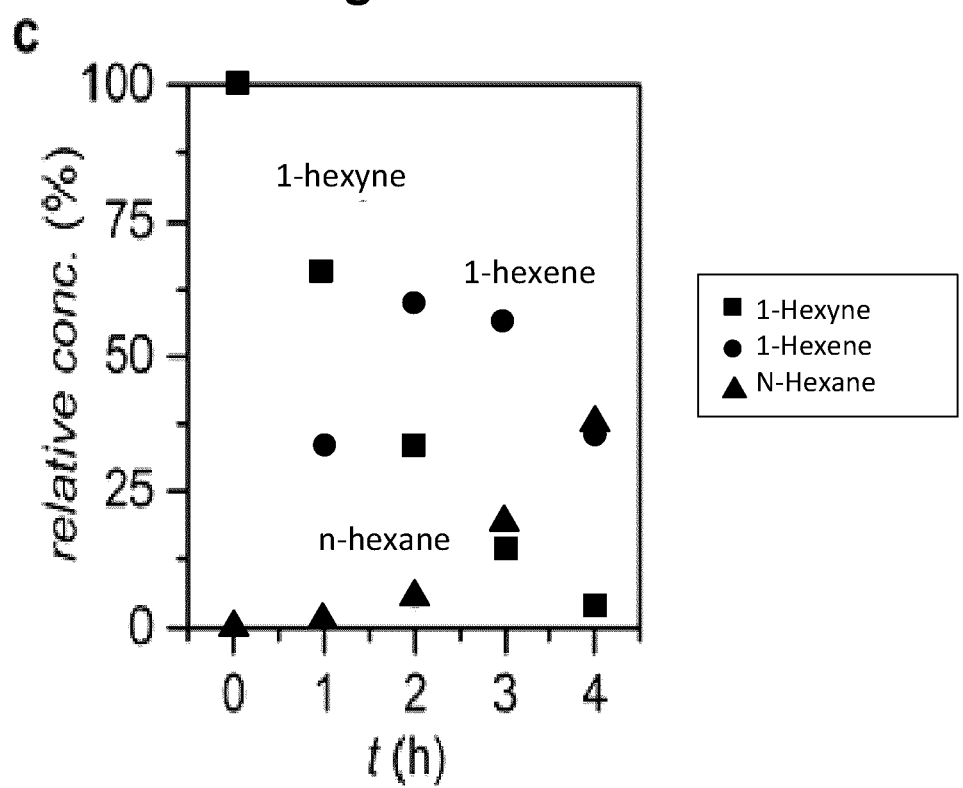
FIG. 11B is a graph showing the relative concentrations of each of 1-hexyne, hexenes isomers and n-hexane during the hydrogenation reaction of 1-hexyne over the course of 4 hours at an applied current of 75 mA. A pentane solvent and 1 M $KHCO_3$ electrolyte were used along with a Pt anode and an Ag/AgCl reference electrode.

Paired electrolysis was then performed at applied currents of 25 and 75 mA to determine the effect of applied current on efficiency, selectivity and reaction rate. Referring to FIGS. 10A and 10B, the reaction rates of both reactions decreased at 25 mA applied current. Referring to FIGS. 11A and 11B, the reaction rates increased at 75 mA applied current.

Figure 12A:
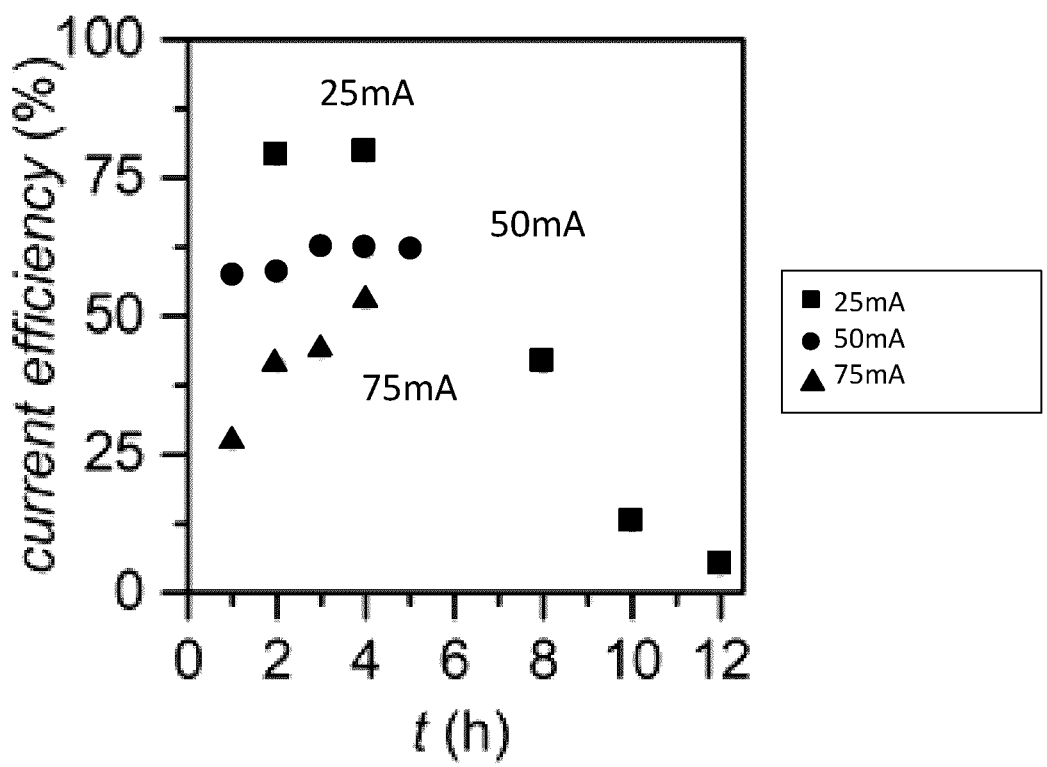
FIG. 12A is a graph showing the current efficiencies for anisaldehyde formation in the alcohol oxidation reaction of anisyl alcohol at applied currents of each of 25, 50 and 75 mA.
Figure 12B:
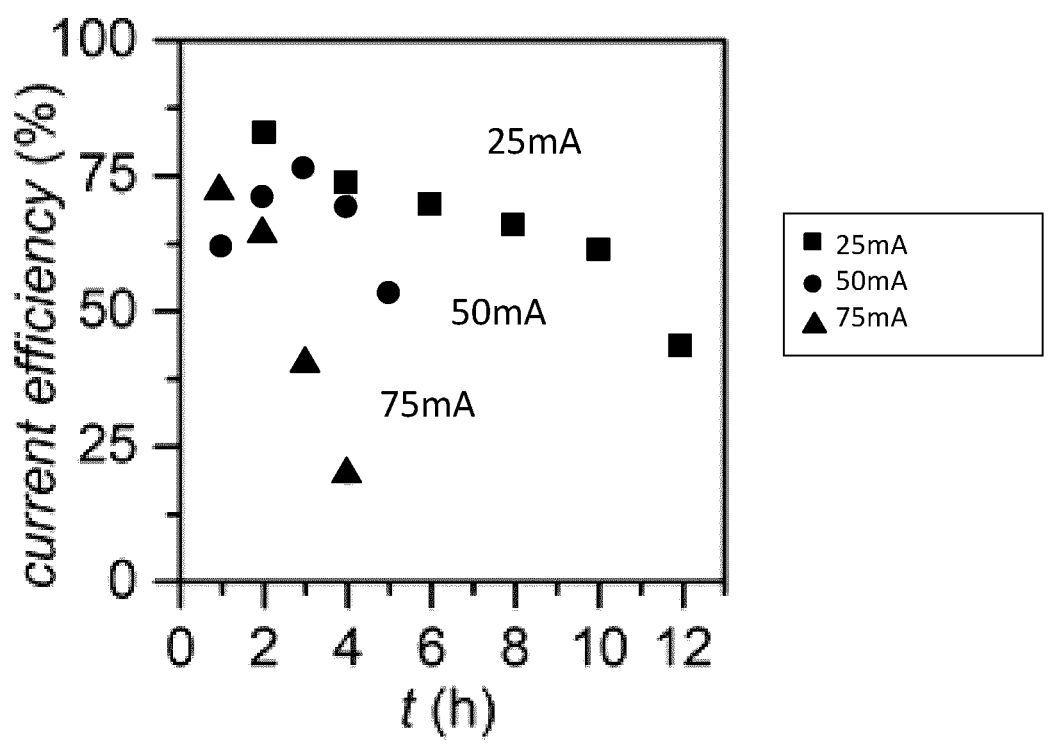
FIG. 12B is a graph showing the current efficiencies for 1-hexene formation in the hydrogenation reaction of 1-hexyne at applied currents of each of 25, 50 and 75 mA.

The current efficiencies for 1-hexane and anisaldehyde show the opposite trend to reaction rates. The current efficiencies generally decreased with increased applied current (see FIGS. 12A and 12B). The inventors have observed the general trend that current efficiencies begin to decrease at longer time points. The decrease in current efficiencies over time may be ascribed to diminishing reactant concentrations.

Example 4—Tunable Reaction Selectivity

It is known that both the alcohol oxidation product and the alkyne hydrogenation product could be further converted to another product. It is desirable to achieve tunable selectivity for both reactions, where the single reduction or oxidation product can be achieved in the short term and a double reduction or oxidation product can be achieved in the long term.

The selectivities of the hydrogenation and oxidation reactions were tested at three applied currents (25, 50 and 75 mA). The alcohol oxidation reaction produced 95-98% anisaldehyde before the production of anisic acid at all three currents.

Figure 13A:
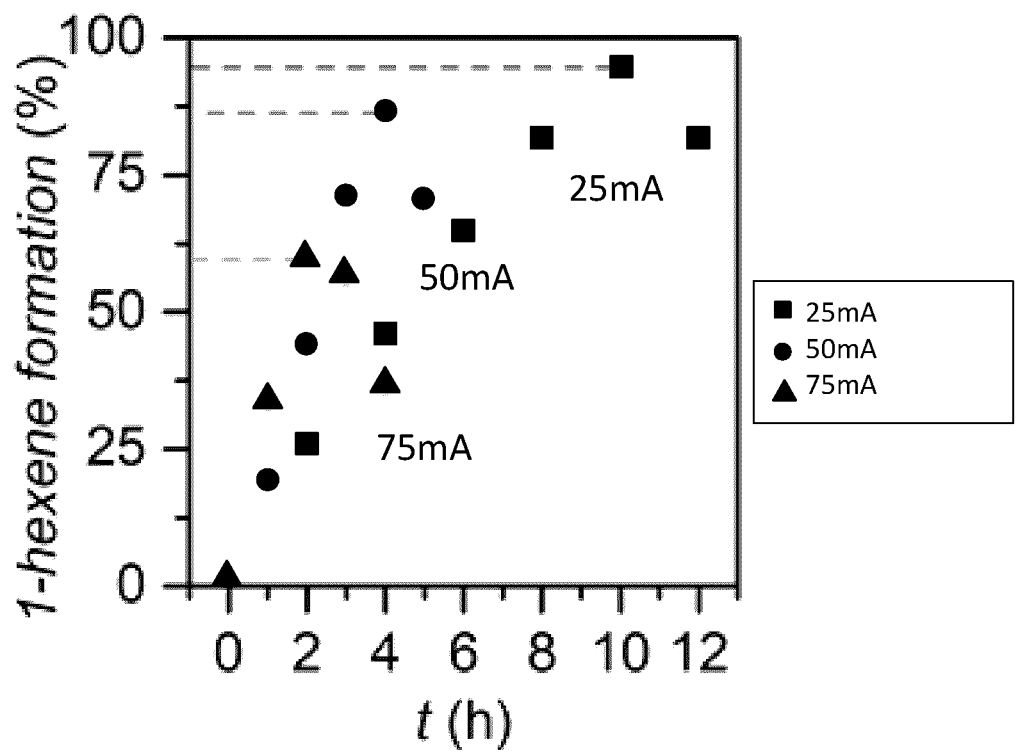
FIG. 13A is a graph showing the percentage of 1-hexene product formation of the hydrogenation reaction at applied currents of 25, 50 and 75 mA in 1 M $KHCO_3$ electrolyte over the course of a 12 hour experiment.

Referring to FIG. 13A, the selectivity of the cathodic hydrogenation reaction varied with a change in applied current. The 1-hexane product was formed with a 95% yield before the formation of n-hexane at 25 mA applied current, but only 60% was formed at 75 mA applied current.

Figure 13B:
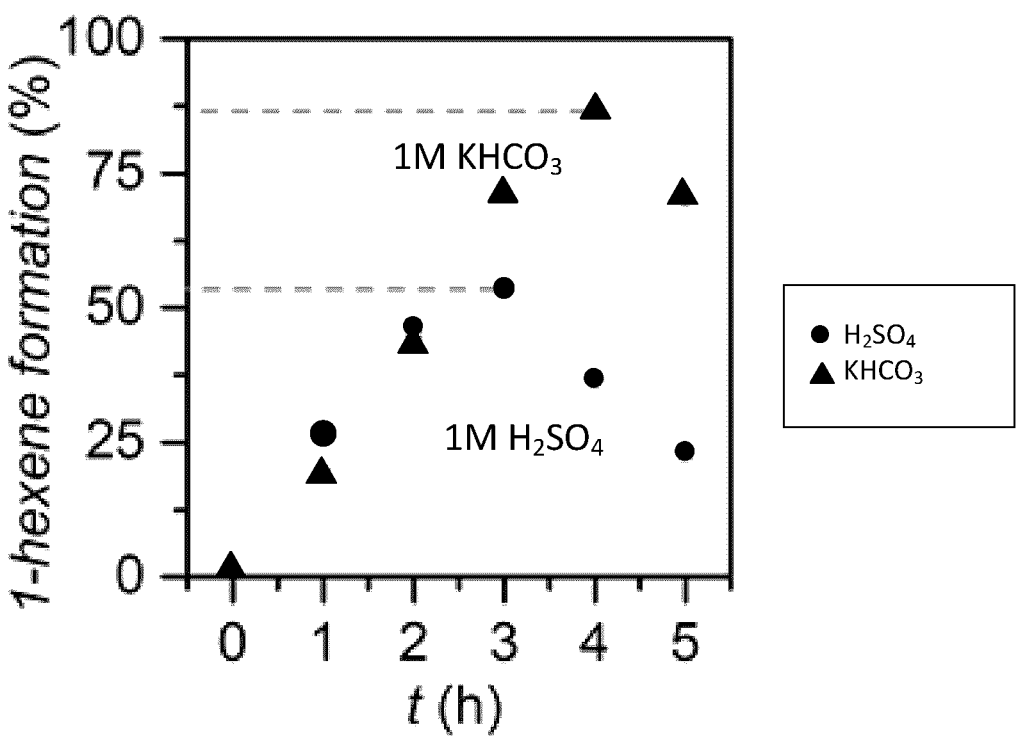
FIG. 13B is a graph showing the percentage of 1-hexene product formation of the hydrogenation reaction at an applied current of 50 mA in one of 1 M $KHCO_3$ or 1 M $H_2SO_4$ electrochemical electrolyte over the course of a 5 hour experiment.

The choice of electrolyte in the electrochemical compartments was also found to affect hydrogenation selectivity. Referring to FIG. 13B, the hydrogenation product 1-hexene was produced with a 56% yield before the onset of n-hexane production in the case where 1 M $H_2SO_4$ was used as the electrolyte on the electrochemical side of the foil. By contrast, 85% 1-hexene could be produced when 1 M $KHCO_3$ was used as the electrolyte. This broad selectivity range (30-35%) that is made accessible by simply changing the applied current and electrolyte usually require fundamental changes in the catalyst rather than the simple modifications to reaction conditions. Without being bound to any particular theory, the inventors hypothesized that the change in selectivity seen from varying electrolyte and applied current is attributed to different hydrogen absorption characteristics of the system under these varying conditions. Both the electrolyte pH and the applied current have been shown to affect proton reduction rate at the surface of the palladium which will affect absorption.

Interpretation of Terms

Unless the context clearly requires otherwise, throughout the description and the claims:
"comprise", "comprising", and the like are to be construed in an inclusive sense, as opposed to an exclusive or exhaustive sense; that is to say, in the sense of "including, but not limited to";
"connected", "coupled", or any variant thereof, means any connection or coupling, either direct or indirect, between two or more elements; the coupling or connection between the elements can be physical, logical, or a combination thereof;
"herein", "above", "below", and words of similar import, when used to describe this specification, shall refer to this specification as a whole, and not to any particular portions of this specification;
"or", in reference to a list of two or more items, covers all of the following interpretations of the word: any of the items in the list, all of the items in the list, and any combination of the items in the list;
"approximately" means a slight variation from the specified value, preferably within plus or minus 5 percent of the specified value unless otherwise specified;
"about" means a slight variation from the specified value, preferably within plus or minus 10 percent of the specified value unless otherwise specified;
the singular forms "a", "an", and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

"Selectivity" refers to the product selectivity of a reaction. Selectivity is measured by the ratio of the desired product formed to the undesired product(s) formed. For example, if a particular reaction yields 4 moles of a desired product and 3 moles of undesired products then the reaction has a selectivity of 4/3. Higher selectivity is generally better.

"current efficiency" or "faradaic efficiency" refers to the proportion of the electrons delivered to or removed from an electrode that yield a desired product as opposed to an electrochemical side reaction such as hydrogen evolution or oxygen evolution. For example, consider the case where the half reaction to yield a product at the cathode of a cell requires one electron. In an ideal case, one mole of product would be generated for each 96485 Coulombs of electrons that pass through the cathode (since Faraday's constant is approximately 96485 C $mol^{-1}$). Suppose that only 0.2 moles of the product is created for each 96485 Coulombs of electrons with the electrons which do not participate in creating the desired product instead participating in side reactions such as hydrogen gas formation. In this example the current efficiency of the cathode reaction for yielding the product would be 20%.

"Hydrogen" is any isotope of the element with atomic number 1.

"Hydrogen ion" is ionized hydrogen ($H^+$). A proton is an example of a hydrogen ion.

"Hydrogenation" includes any reaction between hydrogen atoms or hydrogen molecules ($H_2$) and a reactant. Hydrogenation includes reactions which add hydrogen to unsaturated organic compounds. For example, a hydrogenation reaction may reduce a double or triple bond in a hydrocarbon. In some embodiments the reactions described herein occur without $H_2$ participating in the reactions.

While processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

In addition, while elements are at times shown as being performed sequentially, they may instead be performed simultaneously or in different sequences. It is therefore intended that the following claims are interpreted to include all such variations as are within their intended scope.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

Various features are described herein as being present in "some embodiments". Such features are not mandatory and may not be present in all embodiments. Embodiments of the invention may include zero, any one or any combination of two or more of such features. This is limited only to the extent that certain ones of such features are incompatible with other ones of such features in the sense that it would be impossible for a person of ordinary skill in the art to construct a practical embodiment that combines such incompatible features. Consequently, the description that "some embodiments" possess feature A and "some embodiments" possess feature B should be interpreted as an express indication that the inventors also contemplate embodiments which combine features A and B (unless the description states otherwise or features A and B are fundamentally incompatible).

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. A method for performing coupled chemical and electrochemical reactions, the method comprising:

applying a current and/or an electrical potential between an anode and a hydrogen selective first membrane;

oxidizing, at the anode, a second reactant to form one or more oxidized products and one or more hydrogen ions;

transporting the hydrogen ions through an ion exchange membrane to the first membrane;

at the first membrane, reducing the hydrogen ions to form hydrogen atoms, wherein the first membrane comprises a non-porous hydrogen selective layer adapted to block the hydrogen ions from diffusing through the first membrane and to selectively allow passage of the hydrogen atoms;

diffusing the hydrogen atoms through the first membrane into a first reaction chamber; and chemically reacting the hydrogen atoms with a first reactant at the first reaction chamber.

2. The method according to claim 1 wherein reacting the hydrogen atoms with the first reactant is performed at a temperature of 100 Celsius or lower.

3. The method according to claim 1 wherein reacting the hydrogen atoms with the first reactant is performed in a first solvent and oxidizing the second reactant is performed in a second solvent different from the first solvent.

4. The method according to claim 3 wherein the first solvent is an organic solvent and the second solvent is a protic solvent or an aqueous solvent.

5. The method according to claim 1 wherein the first reactant comprises a double bond or a triple bond and reacting the hydrogen atoms with the first reactant comprises reducing the double bond or a triple bond.

6. The method according claim 1 wherein the ion exchange membrane blocks the second reactant and oxidized products from reaching the first membrane.

7. The method according to claim 1 wherein reacting the hydrogen atoms with the first reactant comprises performing a hydrogenation reaction.

8. The method according to claim 1 comprising performing an electrochemical organic oxidation reaction at the anode.

9. The method according to claim 1 wherein the first reactant comprises an unsaturated organic molecule.

10. The method according to claim 9 wherein the unsaturated organic molecule comprises an alkene or an alkyne.

11. The method according to claim 1 wherein the non-porous hydrogen selective layer comprises a dense metallic hydrogen selective layer.

12. The method according to claim 1, wherein the non-porous hydrogen selective layer comprises a layer of palladium or a palladium alloy.

* * * * *